United States Patent
Murakami et al.

[11] Patent Number: 6,057,684
[45] Date of Patent: May 2, 2000

[54] MAGNETIC FLAW DETECTION APPARATUS USING AN E-SHAPED MAGNETIC SENSOR AND HIGH-PASS FILTER

[75] Inventors: Yoshihiro Murakami, 17-15, Kamitoda 2-chome, Toda-shi, Saitama; Akio Nagamune, Tokyo; Hiroharu Kato, Tokyo; Junichi Yotsuji, Tokyo; Kozo Maeda, Tokyo; Kenichi Iwanaga, Tokyo, all of Japan

[73] Assignees: Yoshihiro Murakami, Toda; NKK Corporation, Tokyo, both of Japan

[21] Appl. No.: 08/860,122

[22] PCT Filed: Oct. 31, 1996

[86] PCT No.: PCT/JP96/03193

§ 371 Date: Jun. 27, 1997

§ 102(e) Date: Jun. 27, 1997

[87] PCT Pub. No.: WO97/16722

PCT Pub. Date: May 9, 1997

[30] Foreign Application Priority Data

Oct. 31, 1995 [JP] Japan .................................... 7-283874
Nov. 17, 1995 [JP] Japan .................................... 7-300064
Nov. 17, 1995 [JP] Japan .................................... 7-300065

[51] Int. Cl.$^7$ ............................ G01N 27/83; G01R 33/12
[52] U.S. Cl. ............................ 324/240; 324/225; 324/242
[58] Field of Search .......................... 324/209, 225–228, 324/234, 235, 239–243

[56] References Cited

U.S. PATENT DOCUMENTS

| | | | |
|---|---|---|---|
| 3,714,558 | 1/1973 | Swanepoel | 324/225 |
| 4,096,437 | 6/1978 | Kitzinger et al. | 324/235 X |
| 4,427,940 | 1/1984 | Hirama et al. | 324/240 |
| 5,191,285 | 3/1993 | Ghostine et al. | 324/225 |
| 5,262,722 | 11/1993 | Hedengren et al. | 324/242 |
| 5,357,198 | 10/1994 | Ando et al. | 324/242 |
| 5,502,382 | 3/1996 | Ando et al. | 324/242 |
| 5,512,821 | 4/1996 | Ando et al. | 324/225 |

FOREIGN PATENT DOCUMENTS

| | | |
|---|---|---|
| 0523249 | 1/1993 | European Pat. Off. . |
| 0 544 911 | 6/1993 | European Pat. Off. . |
| 2 274 917 | 1/1976 | France . |
| 25 26 978 | 1/1976 | Germany . |
| 253685 | 1/1988 | Germany ............................. 324/209 |
| 50-11087 | 2/1975 | Japan . |
| 51-14091 | 2/1976 | Japan . |
| 1-072052 | 3/1989 | Japan . |
| 64-72052 | 3/1989 | Japan . |
| 4-86552 | 3/1992 | Japan . |
| 4-30540 | 7/1992 | Japan . |
| 4-348272 | 12/1992 | Japan . |
| 7-225220 | 8/1995 | Japan . |
| 8-193980 | 7/1996 | Japan . |
| 1 498 218 | 1/1978 | United Kingdom . |
| 2 262 346 | 6/1993 | United Kingdom . |
| WO 92/14145 | 8/1992 | WIPO . |

*Primary Examiner*—Gerard Strecker
*Attorney, Agent, or Firm*—Eugene Lieberstein; Michael N. Meller

[57] ABSTRACT

A magnetic sensor in which magnetic leakage flaw detection can be performed with high accuracy without so reducing liftoff, and a magnetic flaw detection method and apparatus to which the magnetic sensor is applied. The magnetic sensor 50 for detecting magnetic flux generated due to a defect portion of a magnetized subject to be inspected has an E-shaped core 51 having magnetic poles (51a, 51b and 51c) arranged in the neighborhood of a steel plate (13) to be inspected, and a search coil (52) wound on the center magnetic pole (51b) of the E-shaped core for detecting the magnetic flux. An external magnetic field floating in the circumference of the E-shaped magnetic sensor passes through the opposite side magnetic poles (51a and 51c) of the E-shaped core 51 but does not cross the center magnetic pole (51b) of the E-shaped core. Accordingly, no voltage due to the external magnetic field is induced in the search coil (52), so that only the magnetic flux caused by the defect portion is detected. Accordingly, the directivity with respect to the external magnetic field is improved so that the generation of a noise voltage due to the external magnetic field is suppressed and S/N at the time of flaw detection is improved.

14 Claims, 21 Drawing Sheets

FIG. 1
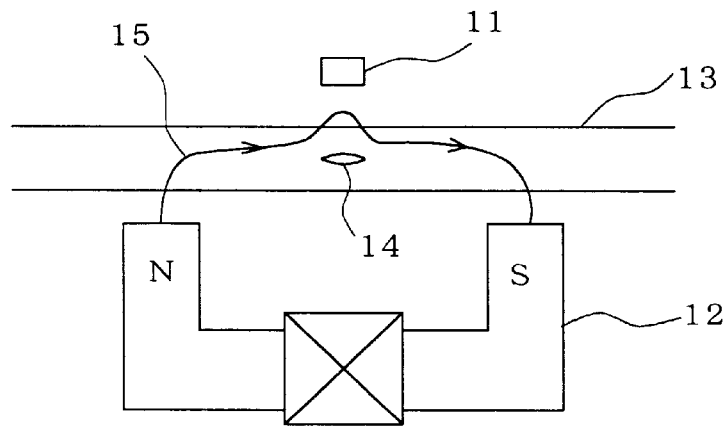
FIG. 2
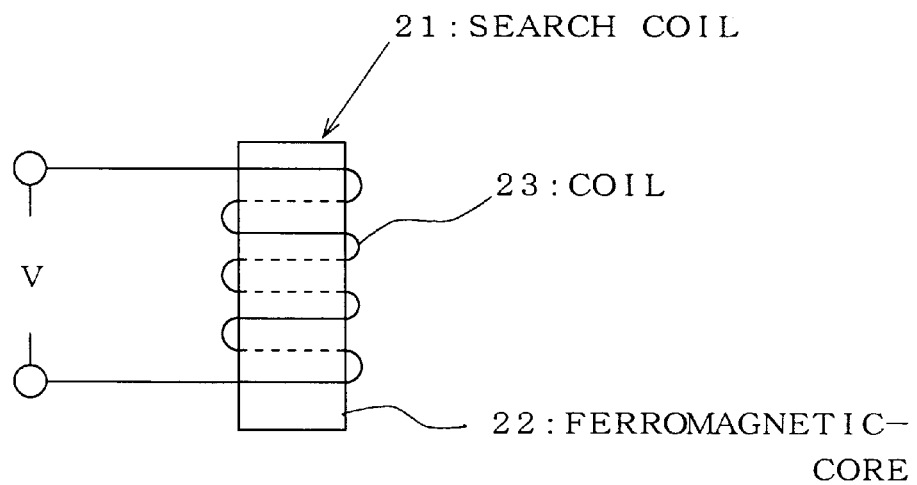
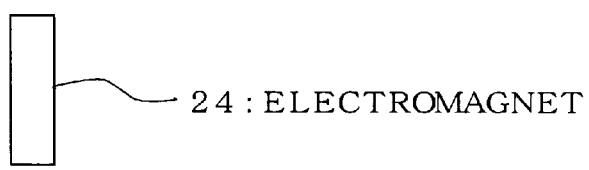

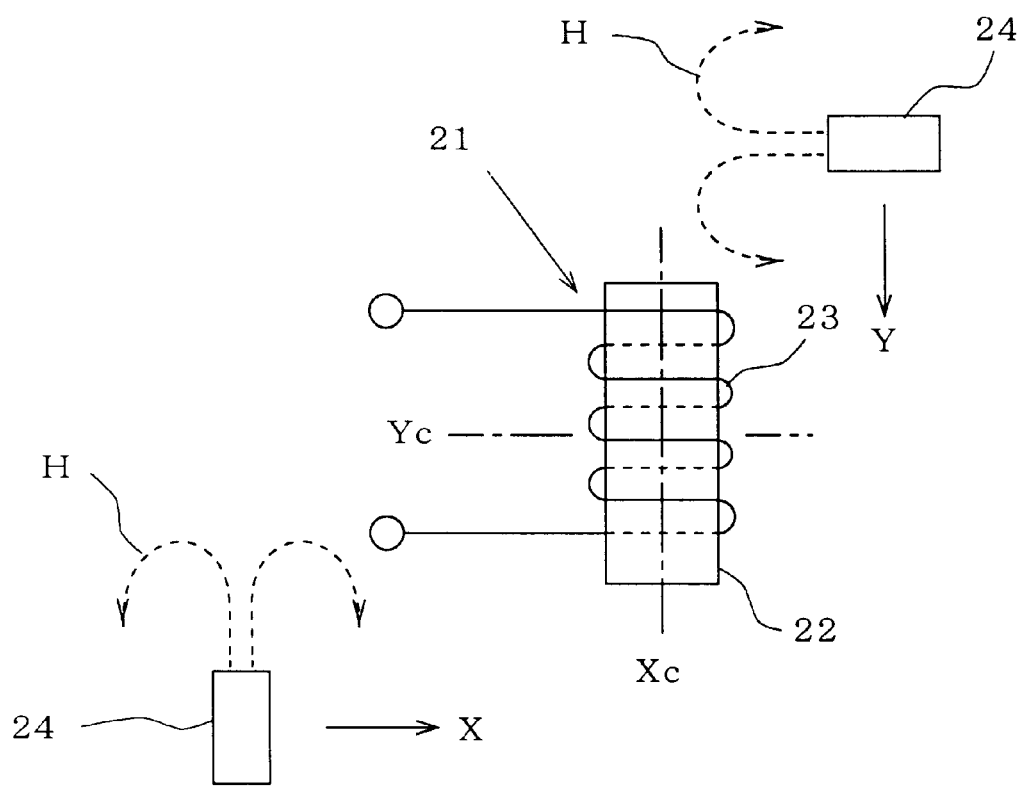
FIG·3

FIG·7
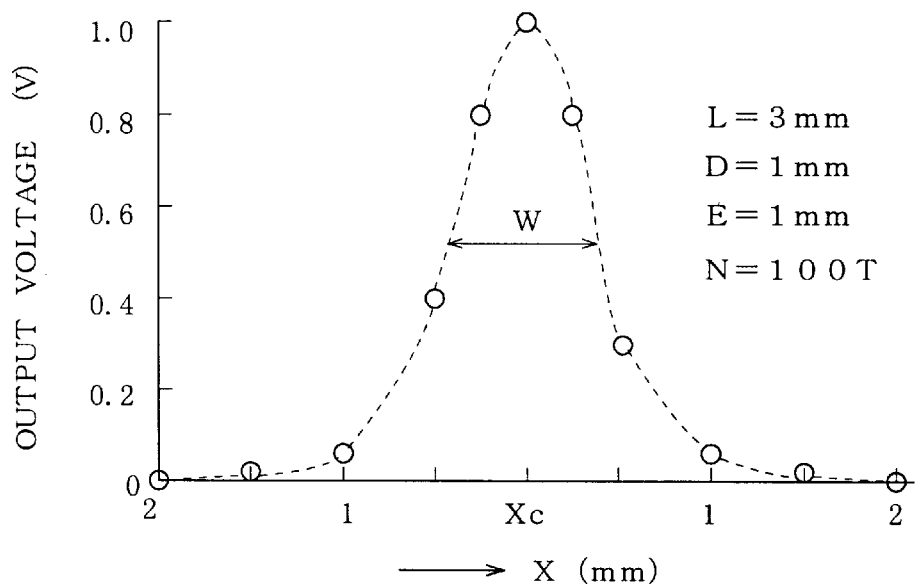
FIG·8
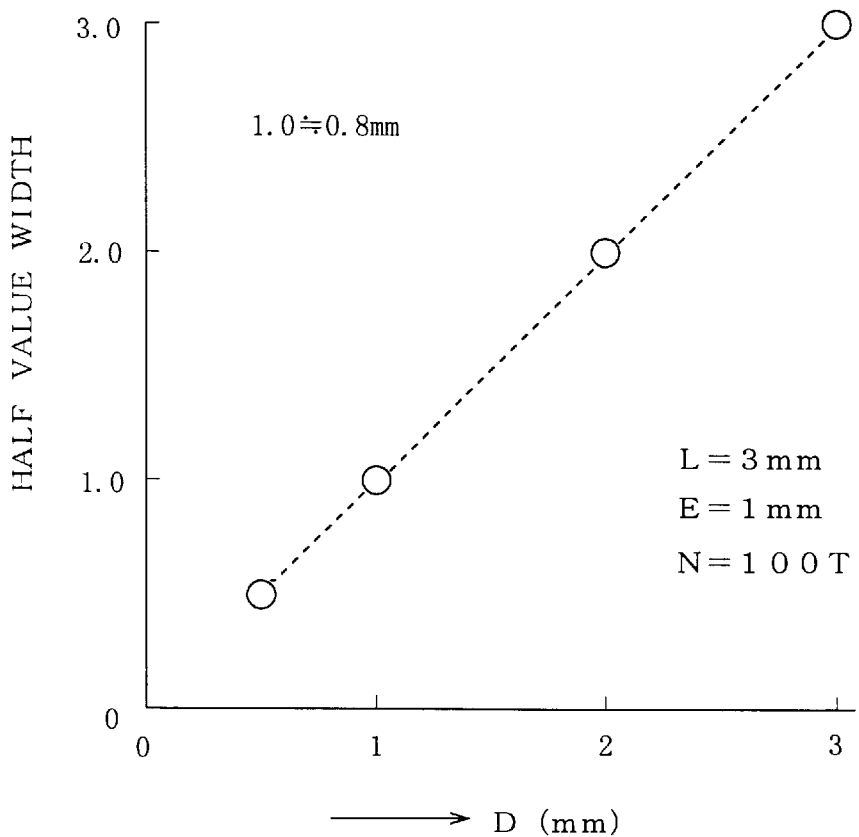

FIG·9
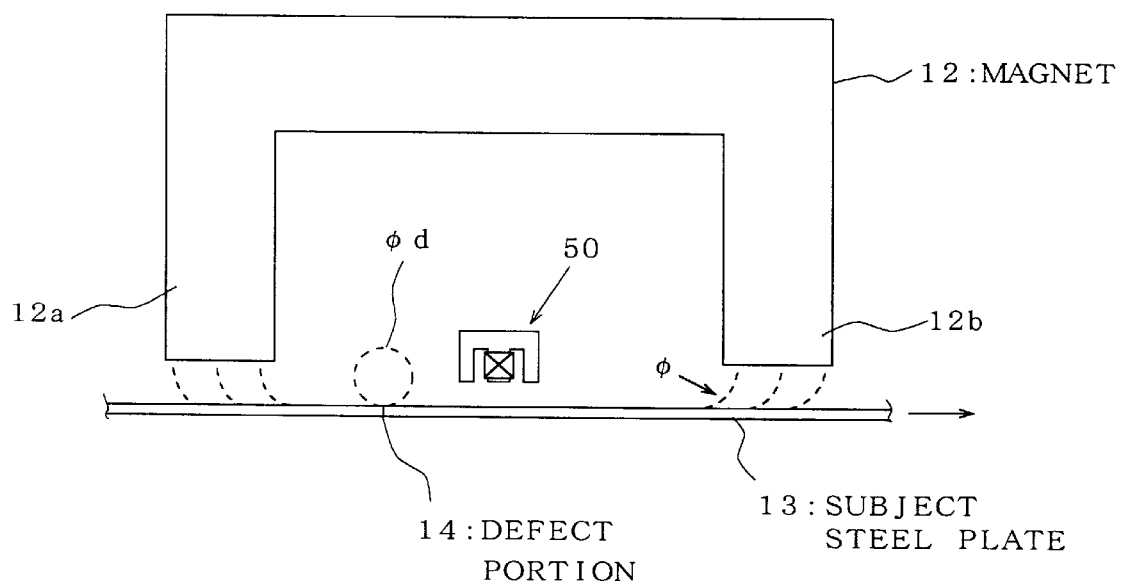

I1 : 0.3 (φmm)
I2 : 0.2
I3 : 0.1

FIG·15
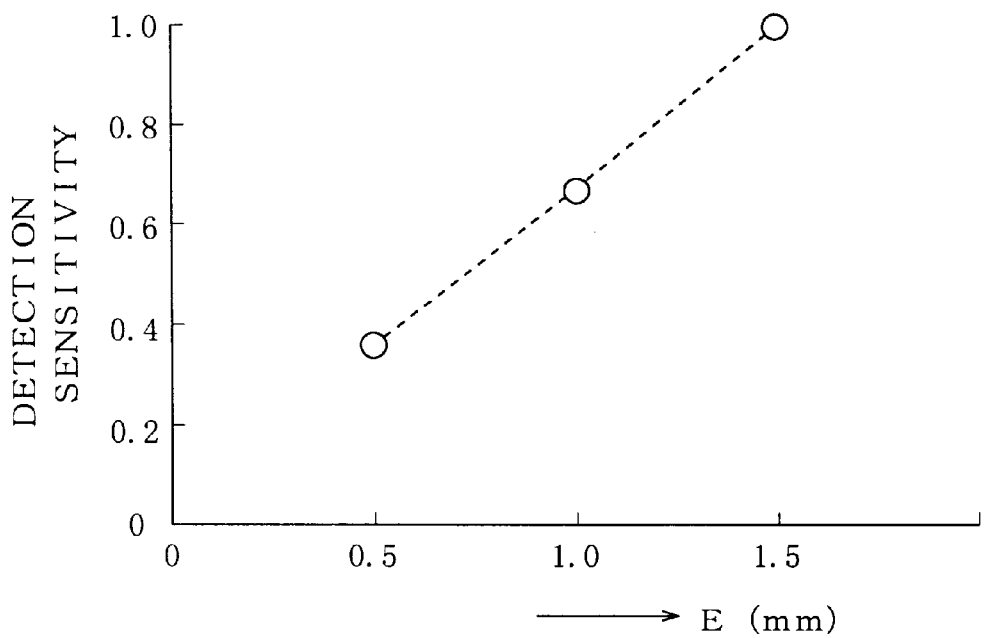
FIG·16
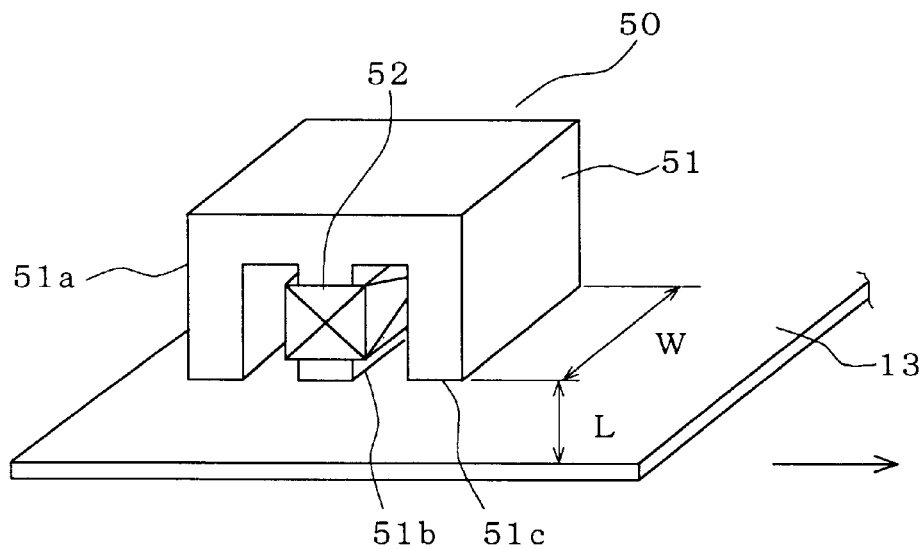

FIG·20
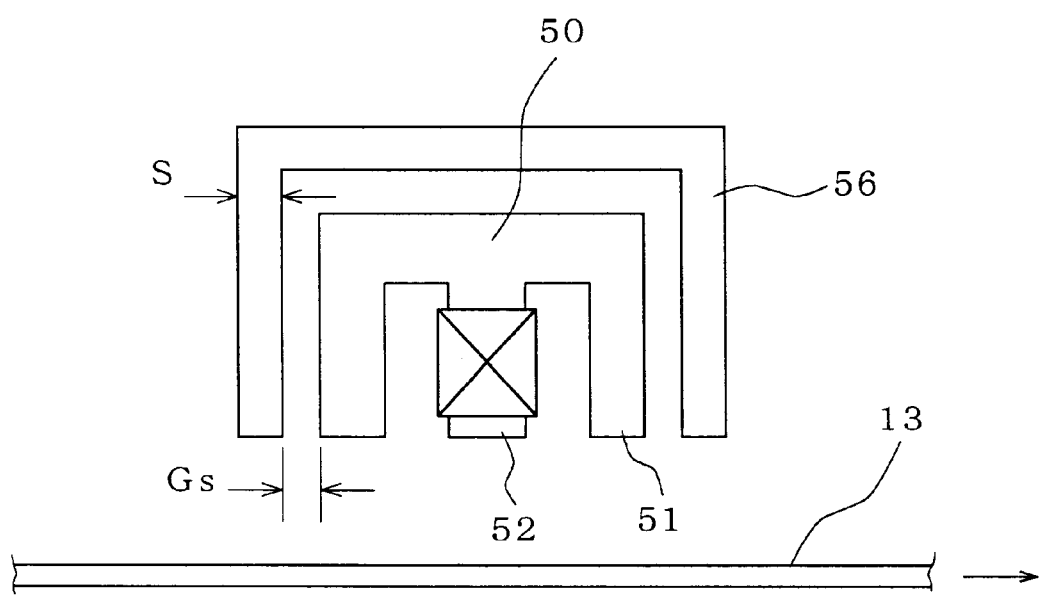

MAGNETIC FLAW DETECTION APPARATUS USING AN E-SHAPED MAGNETIC SENSOR AND HIGH-PASS FILTER

TECHNICAL FIELD

The present invention relates to a magnetic sensor for detecting a micro defect portion such as a flaw, or the like in a ferromagnetic subject to be inspected such as various steel plate, pipe, bar materials or the like, by a magnetic leakage method, and a magnetic flaw detection apparatus using such a magnetic sensor.

BACKGROUND ART

A magnetic leakage method is widely used as a method for detecting a defect in a magnetic substance such as a steel belt. The theory thereof is shown in FIG. 1. In FIG. 1, the reference numeral 11 designates a magnetic sensor; 12, a magnetizer; 13, a subject to be inspected such as a steel belt or the like; 14, a defect; and 15, magnetic flux. The subject 13 is magnetized by the magnetizer 12. A large part of the magnetic flux generated by the magnetizer 12 passes through the subject 13 which is small in magnetic reluctance. If there is a defect 14 in the subject 13, the passage of the magnetic flux is, however, impeded by the defect 14 so that a part of the magnetic flux leaks into air. This leakage flux is detected by the magnetic sensor 11 to thereby detect the presence of a defect 14.

A Hall device, a magnetic reluctance device, a magnetic semiconductor device or the like, is used as the magnetic sensor 11. As other examples of the magnetic sensor, a magnetic flaw detection coil constituted by a coil wound on a cylindrical iron core as disclosed in Japanese Patent Unexamined Publication No. Sho-59-160750, or a magnetic flaw detection coil constituted by a coil wound on a ferromagnetic core which coil is supplied with an alternating current to thereby detect the difference between a positive side voltage and a negative side voltage generated across the opposite ends of the flaw detection coil, as disclosed in Japanese Patent Unexamined Publication No. Hei-2-162276 is used.

FIG. 2 is an explanatory view for explaining the operation of a conventional flaw detection coil (search coil). As shown in the drawing, a search coil 21 is constituted by a ferromagnetic core 22, and a coil 23 wound on the core 22. A voltage V which is induced, for example, when an electromagnet 24 is made to approach the search coil 21 so as to make alternating magnetic flux cross the core, is expressed by the following expression (1):

$$V = \frac{d\phi}{dt} = \mu_2 \cdot N \cdot S \frac{dH}{dt} \quad (1)$$

in which $\mu_2$ is the effective magnetic permeability of the ferromagnetic core 22, H is the intensity of a magnetic field crossing the ferromagnetic core 22, N is the number of turns of the coil 23, S is the sectional area of the ferromagnetic core 22, and $\phi$ is the magnetic flux crossing the ferromagnetic core 22.

As is obvious from the expression (1), a voltage V proportional to the intensity H of a magnetic field crossing the ferromagnetic core 22 and the change of the intensity of a magnetic field at intervals of a unit time is induced in the coil 23 when the sectional area S of the ferromagnetic core 22, the effective magnetic permeability $\mu_2$ thereof and the number of turns N of the coil are fixed.

The outline of a voltage V induced in the coil 23 in the conventional search coil 21 at the time when the position of the search coil 21 relatively changes to the electromagnet 24 will be described below.

FIG. 3 is a typical view for explaining a voltage induced in the search coil at the time when the position of the search coil relatively changes to the electromagnet. FIGS. 4A and 4B are characteristic graphs of the detection sensitivity of the search coil at the time when the position of the search coil relatively changes to the electromagnet.

When the electromagnet 24 is moved (in the X-axis direction) so as to intersect the center axis Xc of the ferromagnetic core 22 perpendicularly, the voltage V induced in the coil 23 increases as the electromagnet 24 approaches the center axis Xc so that the voltage V is maximized when the electromagnet 24 crosses the center axis Xc and, contrariwise, the voltage V induced in the coil 23 decreases as the electromagnet 24 goes far from the center axis Xc so that normal distribution characteristic is obtained (see FIG. 4A). On the other hand, when the electromagnet 24 is moved (in the Y-axis direction) toward a line Yc perpendicular to the center axis Xc, the voltage V induced in the coil 23 increases before the voltage V reaches a certain point and the voltage V decreases after the voltage V exhibits its maximum so that the voltage V becomes 0 V when the electromagnet 4 crosses the line Yc (see FIG. 4B).

Incidentally, the defect heretofore required to be detected in the thin steel belt is a relatively large defect which is called gouge. With the enlargement of application of such a thin steel belt in the industrial field, the detection of a smaller inclusion has been, however, required recently. For example, an inclusion having a volume not larger than $10^{-3}$ (mm$^3$) has become a subject to be detected. To detect such a micro defect, the magnetic sensor including the aforementioned search coil has the following problems.

(1) A Hall device or a magnetic diode can measure the intensity of a static magnetic field, but cannot be applied to high-accurate magnetic leakage flaw detection because its characteristic varies and the output voltage or the like changes depending on the temperature change.

(2) Further, the conventional search coil is good in temperature characteristic, but an induced voltage V corresponding to the intensity of an external magnetic field is generated in the coil 23 in the up/down direction with respect to the longitudinal direction of the ferromagnetic core 22, and in the outer circumferential direction of the coil 23. Accordingly, a noise voltage due to unnecessary disturbance magnetic flux is induced simultaneously to lower the performance of flaw detection when the search coil is used for magnetic leakage flaw detection as shown in FIGS. 4A and 4B.

(3) Further, in any one of the conventional techniques, the distance (liftoff) between the steel belt and the magnetic sensor is required to be reduced in order to detect a micro defect. As a measure, there is used a method for floating the magnetic sensor in air to keep the liftoff in a small value of about 0.1 (mm) as disclosed in Utility Model Unexamined Publication No. 61-119759. This method, however, has an operational problem since it increases the ppossibility of the magnetic sensor contacting the steel belt, or the like.

(4) If the liftoff is reduced in order to detect a micro defect, the magnetic sensor is easily influenced by disturbance such as vibration of the steel belt or the like, and easily receives background noise (noise due to magnetic distortion, surface roughness, stress distortion, etc. of the steel plate), or the like, caused by the magnetic irregularity of the steel belt. Accordingly, it is difficult to obtain sufficient S/N.

(5) The most part of the frequency component of a defect detection signal overlaps the frequency component of the background noise, so that improvement of S/N cannot be performed sufficiently by means of a filter or the like.

(6) In order to detect a smaller defect, the steel belt is required to be magnetized more intensively so that leakage flux due to the defect is generated efficiently. Floating magnetic flux (magnetic flux reaching a magnetic pole of a magnetizer from another magnetic pole through air) generated in the neighborhood of the steel belt is, however, also increased so that the magnetic sensor may be saturated to bring the lowering of detection sensitivity.

DISCLOSURE OF THE INVENTION

An object of the present invention is to provide a magnetic sensor which can be applied to high-accurate magnetic leakage flaw detection.

Another object of the present invention is to provide a magnetic flaw detection method and apparatus in which high-accurate magnetic leakage flaw detection can be performed.

A further object of the present invention is to provide a magnetic flaw detection method and apparatus in which weak and local leakage flux caused by the micro defect of the subject can be detected efficiently with high S/N without making the liftoff so small.

An E-shaped magnetic sensor according to the present invention is a magnetic sensor for detecting magnetic flux generated due to a defect portion of a magnetized subject to be inspected, comprising: an E-shaped core of a ferromagnetic substance having projecting portions disposed in the neighborhood of the subject; and a search coil wound on a center projecting portion of the E-shaped core, for detecting the magnetic flux. The ferromagnetic substance of the E-shaped core has initial magnetic permeability not smaller than 2000.

In the E-shaped magnetic sensor according to the present invention, the floating external magnetic field in the circumference of the E-shaped magnetic sensor passes through projecting portions at opposite sides of the E-shaped core but does not cross the center projecting portion of the E-shaped core. Accordingly, there is no voltage induced in the search coil by the external magnetic field. Accordingly, directivity against the external magnetic field is improved and the generation of the noise voltage due to the external magnetic field is suppressed, so that improvement of S/N at the time of flaw detection is attained. Furthermore, because the value of initial magnetic permeability of the ferromagnetic substance constituting the E-shaped core is selected to be not smaller than 2000, sensitivity in detection of a weak magnetic field is improved.

According to the present invention, a magnetic flaw detection apparatus comprises: a magnetizer for magnetizing the subject to be inspected; and an E-shaped magnetic sensor including an E-shaped core of a ferromagnetic substance having projecting portions disposed in the neighborhood of the subject, and a search coil wound on a center projecting portion of the E-shaped core for detecting the magnetic flux.

Because the magnetic flaw detection apparatus according to the present invention uses the aforementioned E-shaped magnetic sensor, the influence of a floating magnetic field, background noise and vibration of the subject can be reduced so that the liftoff can be set to be relatively large. Accordingly, inspection can be performed in a stable operation without reduction of the moving speed of the subject.

Furthermore, because the frequency component of the detection signal becomes high, separation from background noise containing a large amount of low frequency component can be performed easily so that improvement of S/N can be achieved.

Another magnetic flaw detection apparatus according to the present invention further comprises a shielding plate of a ferromagnetic substance for magnetically shielding the E-shaped magnetic sensor. By arranging such a shielding plate, the E-shaped magnetic sensor is hardly saturated even in an intensive magnetic field generated by the magnetizer and, accordingly, force of magnetization can be strengthened so that an intensive detection signal is obtained. As a result, detection of a micro inclusion not larger than 10–3 (mm$^3$) can be performed.

Further in another magnetic flaw detection apparatus according to the present invention, the magnetizer has a pair of magnetizing magnetic poles; and the E-shaped magnetic sensor is disposed between the pair of magnetizing magnetic poles.

Another magnetic flaw detection apparatus according to the present invention further comprises a shaft bearing for fixing the magnetizer, and a nonmagnetic roll, inside of which the magnetizer is disposed, rotatably supported by the shaft bearing, wherein the subject is moved on the nonmagnetic roll so that the E-shaped magnetic sensor is disposed oppositely to the nonmagnetic roll through the subject.

Further in another magnetic flaw detection apparatus according to the present invention, the subject is a belt-like material which moves; and a row of three magnetic poles of the E-shaped core is arranged along the direction of the movement of the subject.

Further another magnetic flaw detection apparatus according to the present invention uses an E-shaped magnetic sensor with a magnetic pole distance D and a magnetic pole thickness E which satisfy the following expression:

$$1<(D+E)/L<4$$

where L is a liftoff of the E-shaped core.

Further another magnetic flaw detection apparatus according to the present invention uses an E-shaped magnetic sensor with a sensor width W which satisfies the following expression:

$$1<W/L.$$

Further in another magnetic flaw detection apparatus according to the present invention, the E-shaped core and the magnetic shielding plate are so disposed that a gap Gs between the E-shaped core and the magnetic shielding plate satisfies the following expression:

$$S/10<Gs$$

where S is the thickness of the shielding plate.

Further in another magnetic flaw detection apparatus according to the present invention, E-shaped magnetic sensors are aligned in line in the width direction of a subject to be inspected at intervals of a pitch P1 which satisfies the following expression and outputs of the E-shaped magnetic sensors adjacent to each other are added up so as to be used for defect detection:

$$P1<1.6W$$

where W is the width of each of the E-shaped magnetic sensors.

Further in another magnetic flaw detection apparatus according to the present invention, E-shaped magnetic sensors are disposed zigzag in the width direction of the subject at intervals of a pitch P2 which satisfies the following expression and larger one of outputs of E-shaped magnetic sensors overlapping each other in the width direction is used for defect detection:

$$P2<0.9W$$

where W is the width of each of the E-shaped magnetic sensors.

Another magnetic flaw detection apparatus according to the present invention further comprises a high-pass filter having a cutoff frequency F determined on the basis of the distance between the centers of magnetic poles in the E-shaped magnetic sensor, the liftoff and the moving speed of the subject, for processing an output signal from the E-shaped magnetic sensor. The background noise component is reduced by this high-pass filter, so that the defect can be detected with optimum S/N.

Further in another magnetic flaw detection apparatus according to the present invention, the subject is a running thin steel belt which moves; and the defect portion of the subject is a micro inclusion in the thin steel belt.

Another magnetic flaw detection apparatus according to the present invention further comprises a cutoff frequency setter for receiving the moving speed of the subject or/and the liftoff L (mm) as input values and setting an optimum cutoff frequency of the high-pass filter automatically. Setting in the cutoff frequency setter is changed automatically to obtain an optimum cutoff frequency correspondingly to the distance between magnetic poles, the liftoff and the moving speed of the subject, so that the defect can be always detected with optimum S/N.

Further in another magnetic flaw detection apparatus according to the present invention, the cutoff frequency F is set to be in a range of ±20% with reference to a frequency F (Hz) satisfying the following expression:

$$F=V\times(3188-675L)\times(850+2000/P)/(1.4\times10^7)$$

where P (mm) is the distance between the centers of magnetic poles of the E-shaped magnetic sensor, L (mm) is the liftoff, and V (mm/s) is the moving speed of the subject.

Incidentally, the respective technical grounds of the aforementioned inequalities and equalities will become clear in the following embodiments.

Further a magnetic flaw detection method according to the present invention comprises the steps of: magnetizing a subject to be inspected; and detecting magnetic flux generated in a defect portion of the subject by the magnetization in the preceding step, by means of a search coil of an E-shaped magnetic sensor.

Another magnetic flaw detection method according to the present invention further comprises the step of compensating a signal induced in the search coil, on the basis of the moving speed of the subject.

Further in another magnetic flaw detection method according to the present invention, the compensation is performed so that the signal induced in the search coil is made to be inversely proportional to the moving speed of the subject. By this compensation, a constant defect output can be obtained regardless of the moving speed of the subject.

Further in another magnetic flaw detection method according to the present invention, the subject is magnetized through a nonmagnetic material in the magnetizing step of the subject.

BRIEF DESCRIPTION OF THE DRAWINGS

FIG. 1 is a theoretical view of a magnetic leakage method for detecting a defect in a magnetic substance;

FIG. 2 is an explanatory view for explaining the operation of a conventional flaw detection coil (search coil);

FIG. 3 is a typical view for explaining a voltage induced in the search coil when the position of the search coil is changed relative to the electromagnet;

FIG. 7 is a characteristic graph showing detection sensitivity of the E-shaped magnetic sensor depicted in FIG. 5 when the position of the E-shaped magnetic sensor is changed relative to the electromagnet;

FIG. 8 is a characteristic graph showing the characteristic of the half-value width of an induced voltage when the distance between magnetic poles in the E-shaped core is changed;

FIG. 9 is a configuration view in the case where the E-shaped magnetic sensor of FIG. 5 is used for leakage flux flaw detection;

FIG. 15 is a characteristic graph showing the detection sensitivity of the magnetic sensor versus the magnetic pole distance of the E-shaped core;

FIG. 16 is an external appearance view of the E-shaped magnetic sensor arranged on an upper portion of a steel plate as a subject to be inspected;

FIG. 20 is an explanatory view showing a configuration in which a magnetic shielding plate of a ferromagnetic substance is arranged in the outside of the E-shaped magnetic sensor;

BEST MODE FOR CARRYING OUT THE INVENTION

Figure 4A:
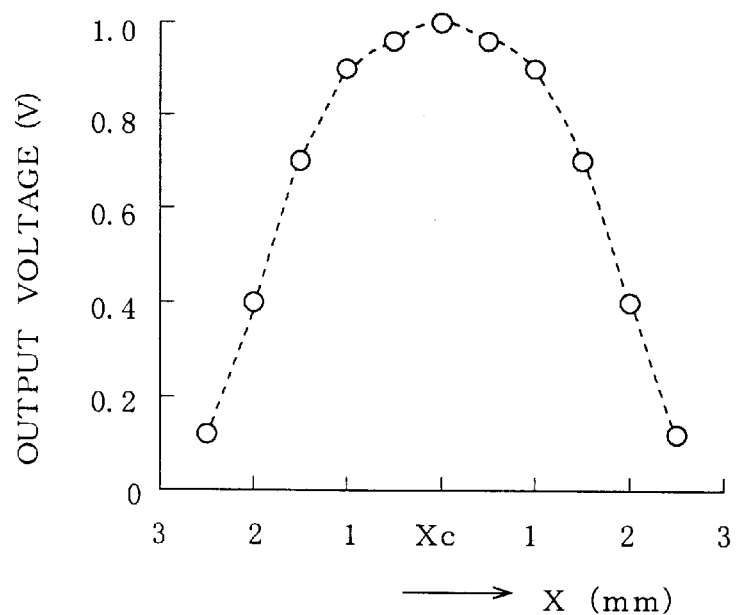
FIGS. 4A and 4B are characteristic graphs of detection sensitivity of the search coil when the position of the search coil is changed relative to the electromagnet.
Figure 4B:
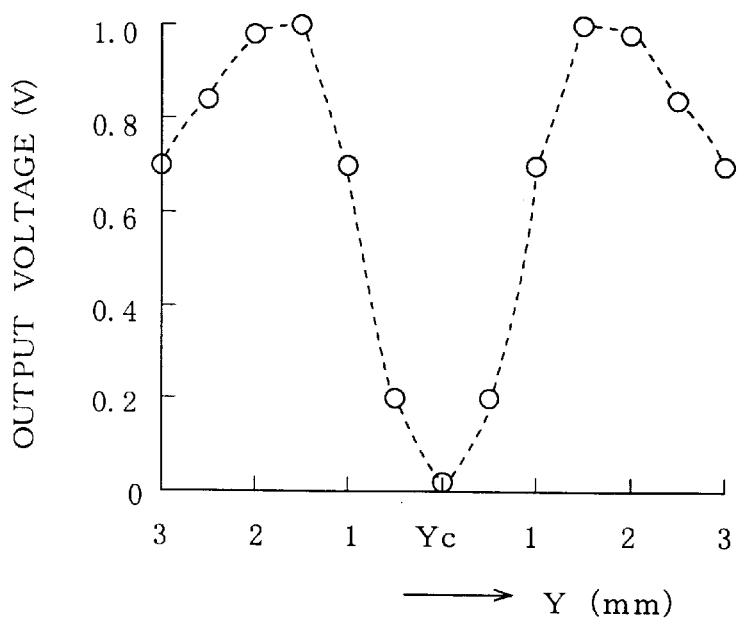
Figure 5:
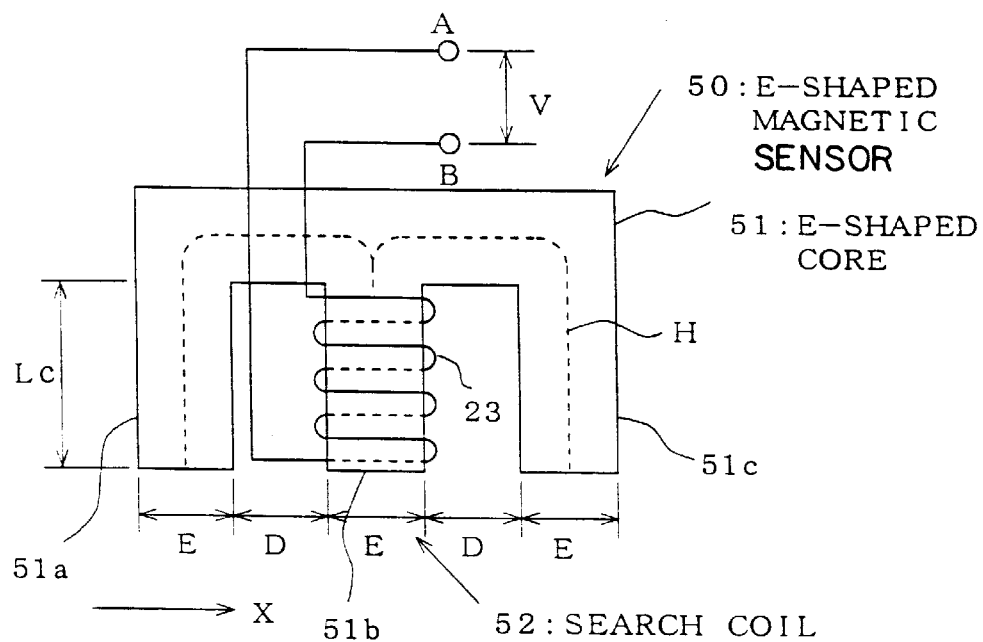
FIG. 5 is a view showing the configuration of an E-shaped magnetic sensor according to an embodiment of the present invention.

FIG. 5 is a view showing the configuration of an E-shaped magnetic sensor according to an embodiment of the present invention. The E-shaped magnetic sensor 50 is constituted by an E-shaped core 51 of a ferromagnetic substance, and a search coil 52 prepared by winding a coil 23 on a center magnetic pole 51b of the E-shaped core 51. Only when an external magnetic field H acts on the center magnetic pole 51b and either one of opposite side magnetic poles 51a and 51c (hereinafter referred to as "left magnetic pole 51a" and "right magnetic pole 51c" respectively) from below, a voltage V corresponding to the intensity of the magnetic field and the change thereof is generated between output ends A and B of the coil 23. Incidentally, a material large in magnetic permeability and small in coercive force, such as a permalloy core, a ferrite core, or the like, is used as the E-shaped core 51 of a ferromagnetic substance. Further, as shown in the drawing, a row of the three poles consisting of the left magnetic pole 51a, the center magnetic pole 51b and the right magnetic pole 51c is arranged along the direction of the movement of a steel plate 13 as a subject to be inspected.

The E-shaped magnetic sensor 50 configured as described above is designed so that an external magnetic field H never crosses the center magnetic pole 51b in the case where the external magnetic field H acts from any positions other than the aforementioned position. This aspect will be described on the basis of a typical view shown in FIG. 6.

Figure 6:
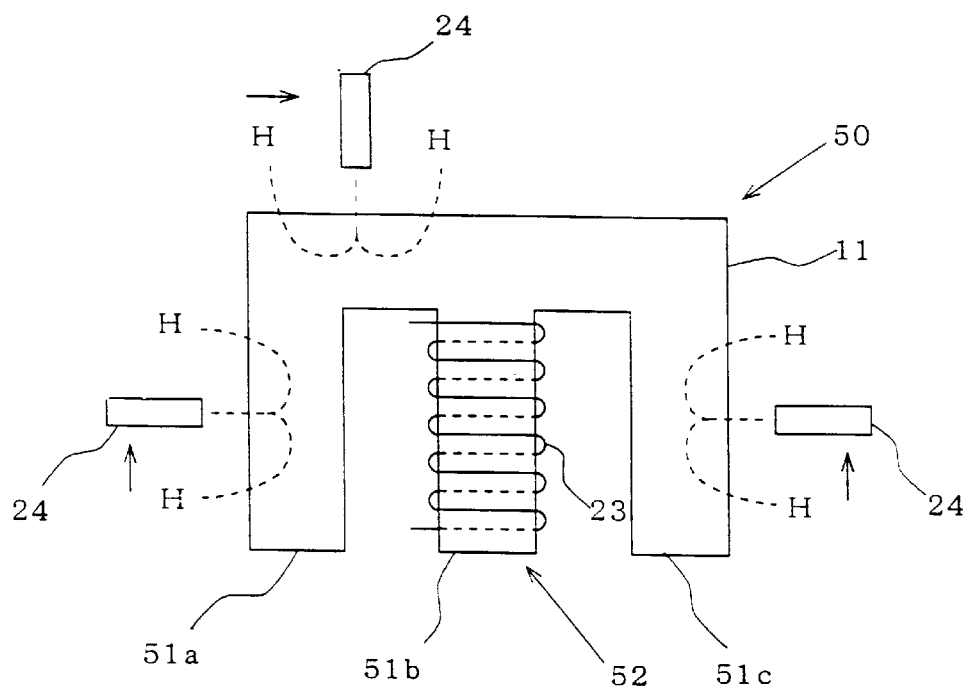
FIG. 6 is a typical view for explaining the operation of the E-shaped magnetic sensor depicted in FIG. 5 when the position of the E-shaped magnetic sensor is changed relative to the electromagnet.

FIG. 6 is a typical view for explaining the operation of the E-shaped magnetic sensor in the case where the position of the E-shaped magnetic sensor is changed relative to the electromagnet. When the relative position of the E-shaped magnetic sensor and the electromagnet is changed, the E-shaped magnetic sensor operates as follows.

(1) When an external magnetic field H generated by the electromagnet 24 acts on the left magnetic pole 51a of the E-shaped core 51, the external magnetic field H crosses the left magnetic pole 51a so as to cooperate with the electromagnet 24 to form a magnetic circuit. In this case, there is no voltage induced in the search coil 52 because the magnetic field H never crosses the center magnetic pole 51b.

(2) Also when an external magnetic field H acts on the right magnetic pole 51c, there is no voltage V generated between output ends A and B of the coil 23 wound on the center magnetic pole 51b because the external magnetic field H never crosses the center magnetic pole 51b in the same manner as described above in the paragraph (1).

(3) Also when an external magnetic field H is made to act on the E-shaped core 11 from above, the external magnetic field H cooperates with the electromagnet 24 to form a magnetic circuit in the same manner as in the aforementioned paragraphs (1) and (2) so that there is no voltage induced in the search coil 52 because the external magnetic field H never crosses the center magnetic pole 51b of the E-shaped core 51. Incidentally, in the case where the external magnetic force H is too intensive in the state of (3) or in the case where the thickness of the core 51 is insufficient, the magnetic field H passes through and crosses the center magnetic pole 51b so that a certain voltage, though it is low, may be induced in the search coil 52.

The detection sensitivity of the E-shaped magnetic sensor 50 will be described below.

FIG. 7 is a characteristic graph showing the detection sensitivity of the magnetic sensor in the case where the position of the E-shaped magnetic sensor relative to the electromagnet is changed. This characteristic graph shows the detection sensitivity in the case where the thickness E of each of the magnetic poles 51a, 51b and 51c in the E-shaped core 51 is 1.0 (mm), the distance D of the magnetic poles is 1.0 (mm), the length Lc of each of the magnetic poles 51a, 51b and 51c is 3.0 (mm) and the number of turns N of the coil 23 is 100T.

As is obvious from this graph, when the electromagnet 24 is moved across the center axis Xc of the center magnetic pole 51b of the E-shaped core 51, the voltage induced in the search coil 52 is maximized at the time when the electromagnet 24 reaches the center axis Xc, and therefore, the output voltage V exhibits an undiffused beam-like characteristic. Further, the half-value width w at −6 dB becomes about 0.8 (mm).

The half-value width of the voltage induced in the search coil 11 in the case where the distance D between the magnetic poles is changed will be described below.

FIG. 8 is a characteristic graph showing characteristic of the half-value width of the induced voltage in the case where the magnetic pole distance of the E-shaped core of the search coil is changed. This characteristic graph shows the characteristic in the case where the thickness E of each of the magnetic poles 51a, 51b and 51c in the E-shaped core 51 is 1.0 (mm), the length Lc of each of the magnetic poles 51a, 51b and 51c is 3.0 (mm), the number of turns N of the coil 3 is 100T, and the magnetic pole distance D is changed to 0.5 (mm), 1.0 (mm), 2.0 (mm) and 3.0 (mm). The half-value width of the voltage induced in the search coil 52 increases as the magnetic pole distance D increases. In this case, the characteristic changes from the undiffused beam-like characteristic to broad characteristic.

It is apparent from the above description that leakage flux generated from a defect can be detected efficiently by setting the magnetic pole distance of the E-shaped core correspondingly to the size of the defect to be detected.

Figure 10A:
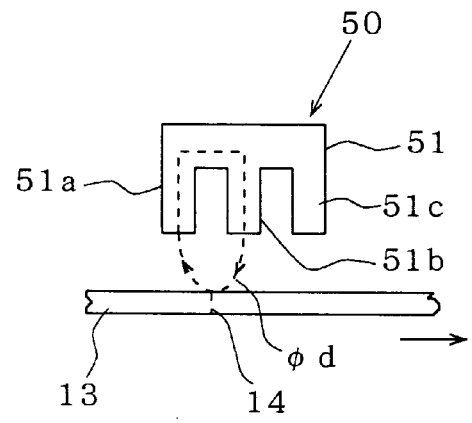
FIGS. 10A to 10C are explanatory views time-serially illustrating crossing of leakage flux generated from a defect portion with respect to poles in the E-shaped core.
Figure 10B:
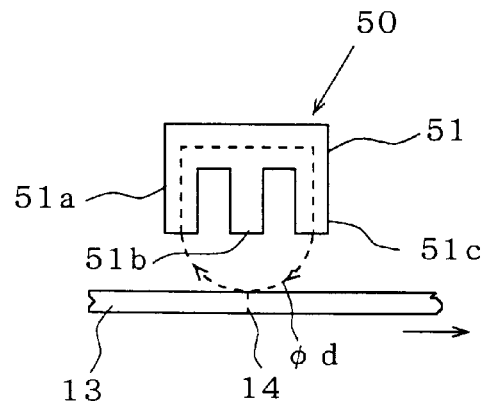
Figure 10C:
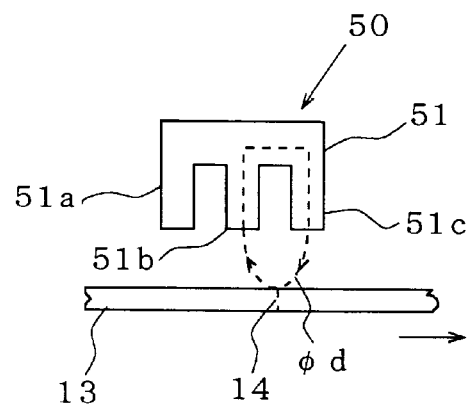

FIG. 9 is a configuration view in the case where the aforementioned E-shaped magnetic sensor is used for leakage flux flaw detection, and FIGS. 10A to 10C are explanatory views which time-serially illustrate crossing of leakage flux generated from a defect portion across the magnetic poles of the E-shaped core. The magnetic sensor 50 is disposed between opposite magnetic poles of the magnet 12, and the respective magnetic poles 51a, 51b and 51c are disposed opposite to the subject steel plate 13.

The operation of the E-shaped magnetic sensor 50 will be described below with reference to FIG. 9 and FIGS. 10A to 10C.

The magnet 12 has a pair of magnetizing magnetic poles 12a and 12b. The E-shaped magnetic sensor 50 is disposed between the magnetizing magnetic poles 12a and 12b. When the subject steel plate 13 is magnetized by the magnetizing magnetic poles 12a and 12b, a local magnetic pole is formed in the defect portion 14 because the magnetic reluctance of the defect portion 14 is larger than that of the normal portion of the base material. Because of the local magnetic pole, magnetic flux φd leaks in the outside of the subject steel plate 13. When the defect portion 14 reaches a center portion between the left magnetic pole 51a and the center magnetic pole 51b in the E-shaped core 51, the leakage flux φd from the defect portion 14 crosses the left magnetic pole 51a and then flows in the center magnetic pole 51b to form a magnetic circuit (see FIG. 10A). In this occasion, a voltage corresponding to the intensity of the leakage flux φd is induced in the search coil 52, so that a voltage V is generated between output ends of the coil 23. When the defect portion 14 comes just under the center magnetic pole 51b of the E-shaped core 51 with the movement of the subject steel plate 13, the leakage flux φd from the defect portion 14 does not cross the center magnetic pole 51b but crosses only the left and right magnetic poles 51a and 51c so that no voltage is induced in the search coil 52 in this condition (see FIG. 10B). When the defect portion 14 then reaches a center portion between the center magnetic pole 51b and the right magnetic pole 51c with the movement of the subject steel plate 13, the leakage flux φd from the defect portion 14 crosses the center magnetic pole 51b and then flows in the right magnetic pole 51c to form a magnetic circuit. In this occasion, a voltage corresponding to the intensity of the leakage flux φd is induced in the search coil 52 in the same manner as described above so that a voltage V is generated between output ends of the coil 23 (see FIG. 10C).

Figure 11A:
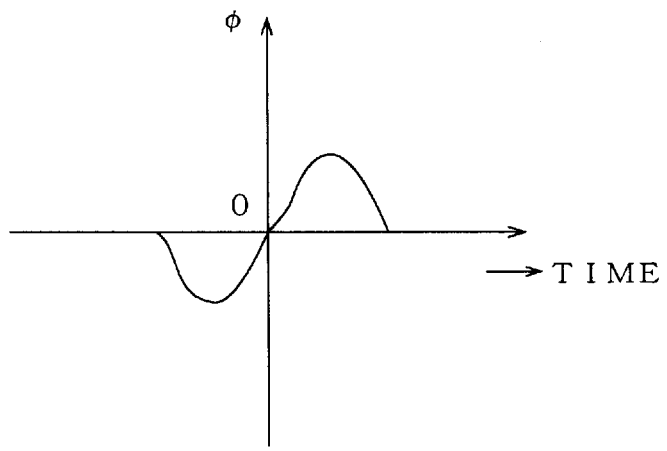
FIGS. 11A and 11B are graphs showing the waveform of magnetic flux crossing the search coil and the waveform of an induced voltage.
Figure 11B:
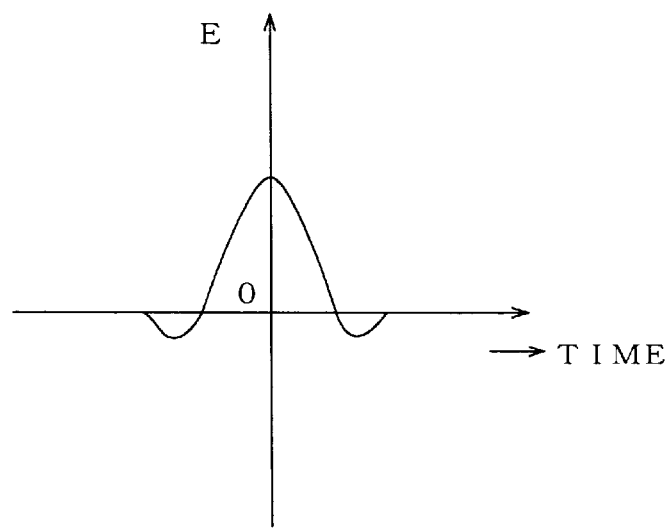

FIGS. 11A and 11B are graphs showing the waveform of magnetic flux crossing the search coil 52 and the waveform of an induced voltage. In the aforementioned series of operations, magnetic flux Φ having a shape shown in FIG. 11A crosses the search coil 52 and a voltage having a waveform as shown in FIG. 11B is induced. The presence of a defect 14 can be detected by detecting the induced voltage.

In the present invention using the aforementioned E-shaped magnetic sensor 50, floating magnetic flux in the neighborhood of the subject steel plate, background noise coming from the outside of the E-shaped magnetic sensor, and so on, pass from the magnetic pole 51a to the magnetic pole 51c directly. Accordingly, there is no influence on the search coil 52, so that noise can be reduced. Further, the change of a magnetic field caused by vibration of the steel belt and vibration of the sensor is canceled by the magnetic circuit constituted by the left and center magnetic poles 51a and 51b and the magnetic circuit constituted by the right and center magnetic poles 51c and 51b, so that the change of a magnetic field can be prevented from being mixed as noise into a signal of the search coil 52.

Accordingly, the defect can be detected with good S/N and the magnetic sensor output is never saturated by the floating magnetic flux even in the case where the liftoff is selected to be not so small. Furthermore, because the frequency component of the defect signal becomes relatively high compared with the frequency component of the background noise, the signal can be separated from noise easily so that the effect of eliminating disturbance noise is improved. Furthermore, by the configuration in which a coil is wound on the center magnetic pole 51b of the E-shaped core 51, the sensitivity characteristic for detection of the external magnetic field is maintained as a undiffused beam-like characteristic, and the sensitivity for detection of a weak magnetic field is improved.

Figure 12:
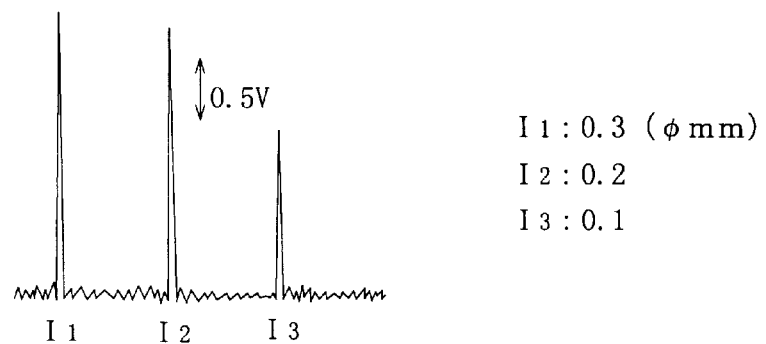
FIG. 12 is a graph showing the amplitude value of an output in the case where a defect portion artificially made in a steel plate as a subject to be inspected is flaw-detected.

FIG. 12 is a graph showing the amplitude values of outputs in the case where defect portions artificially made in a subject steel plate is flaw-detected. FIG. 12 shows test results obtained in the condition in which drill holes having hole diameters of 0.3 φ(mm), 0.2 φ(mm) and 0.1 φ(mm) respectively are made as defect portions $I_1$, $I_2$ and $I_3$ in a subject steel plate 13 having a plate thickness of 0.15 (mm), and the subject steel plate 13 is subjected to leakage flux flaw detection by the magnetic sensor 50. A drill hole having a hole diameter of 0.1 φ(mm) can be detected with S/N not smaller than 10. Incidentally, in FIG. 12, the amplitude value of the output from the defect portion having a hole diameter of 0.3 φmm is expressed so as to be nearly equal to the amplitude value of the output from the defect portion having a hole diameter of 0.2 φ(mm). However, this is because the defect output level is over the set range of a recorder so that the output is saturated and the linear characteristic with respect to the size of the hole diameter of the defect portion 14 is kept.

Figure 13:
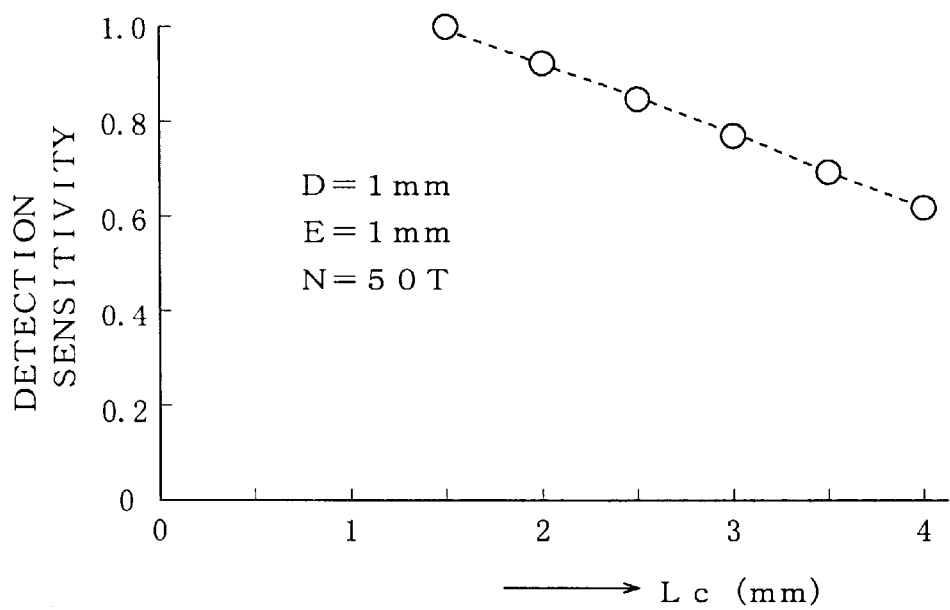
FIG. 13 is a characteristic graph showing the detection sensitivity of the magnetic sensor versus the magnetic pole length of the E-shaped core.

FIG. 13 is a characteristic graph showing the detection sensitivity of the magnetic sensor versus the magnetic pole length of the E-shaped core. This characteristic graph shows the detection sensitivity in the case where a defect portion 14 of a drill hole having a hole diameter of 0.1 φ(mm) made in a subject steel plate 13 shown in FIG. 9 is detected by magnetic sensors 50 using E-shaped cores 11 having different magnetic pole lengths respectively. The magnetic pole length Lc of the E-shaped core 51 is changed so as to be elongated by 0.5 (mm) in a range of from 1.5 to 4.0 (mm). Incidentally, the distance D between the magnetic poles in the E-shaped core 51 is 1.0 (mm), the thickness E of each of the magnetic poles 51a, 51b and 51c is 1.0 (mm) and the number of turns N of the coil is 50 T.

As shown in FIG. 13, the sensitivity for detection of the defect portion 14 formed by a drill hole tends to decrease as the magnetic pole length Lc increases. This reason is that the average length of the magnetic circuit, through which the leakage flux φd generated from the defect portion 14 passes, increases because of the magnetic pole length Lc of the E-shaped core 51, so that reluctance of the magnetic circuit increases. Therefore, shortening the magnetic pole length Lc as much as possible is advantageous, but the magnetic pole length Lc is determined taking account of the technique of coil mounting because the allowed number of turns N of the coil decreases as the magnetic pole length Lc decreases. Further, in the case where the subject steel plate 13 is replaced by a bar material or a pipe as the subject material, the magnetic pole length Lc of the E-shaped core 51 is determined correspondingly to the external shape of the subject material in order to detect the defect portion 14.

Figure 14:
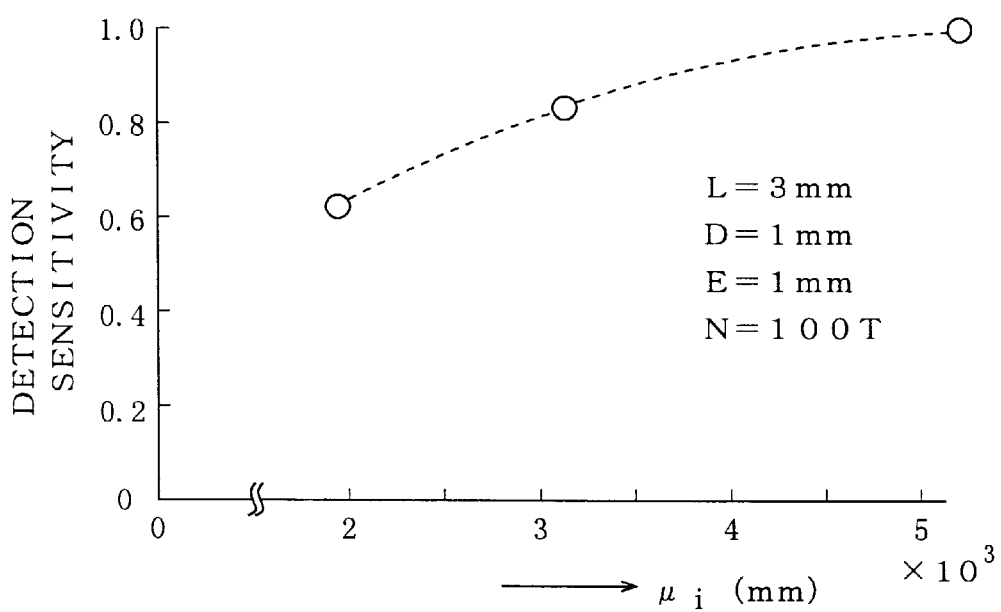
FIG. 14 is a characteristic graph showing the detection sensitivity of the magnetic sensor versus the initial magnetic permeability of the E-shaped core.

FIG. 14 is a characteristic graph showing the detection sensitivity of the magnetic sensor versus the initial magnetic permeability value of the E-shaped core. This graph shows the detection sensitivity of the magnetic sensor 50 in the case where ferromagnetic substances different in initial magnetic permeability $\mu_i$ are used as the E-shaped core 51. The values of initial magnetic permeability $\mu_i$ of the ferromagnetic substances are from about 1800 to about 5500. Incidentally, the length Lc of each of the magnetic poles 51a, 51b and 51c in the E-shaped core 51 is 3.0 mm, the distance D between the magnetic poles is 1.0 (mm), the thickness E of each of the magnetic poles is 1.0 (mm) and the number of turns N of the coil is 100 T.

As shown in FIG. 14, the sensitivity for detection of the artificial defect portion (having a hole diameter of 0.1 φ(mm)) is improved as the value of initial magnetic permeability $\mu_i$ of the E-shaped core 51 increases. This is because magnetic reluctance in the E-shaped core 51 decreases as the initial magnetic permeability $\mu_i$ increases. Specifically, as shown in FIGS. 10A to 10C, there is formed a magnetic circuit in which the magnetic flux φd generated from the defect portion 14 crosses the E-shaped core 51 through an air layer on the subject steel plate 13 and then returns to the subject steel plate 13. The magnetic reluctance $R_\phi$ of the E-shaped core 51 in this magnetic circuit is expressed by the expression (2):

$$R_\phi = \frac{Lav}{\mu_i \cdot S} \quad (2)$$

in which Lav is the average magnetic path length of the E-shaped core 51, $\mu_i$ is the initial magnetic permeability of the E-shaped core 51, and S is the sectional area of the E-shaped core 51.

Accordingly, because the magnetic reluctance $R_\phi$ of the E-shaped core 51 decreases so as to be inversely proportional to the value of initial magnetic permeability $\mu_i$ of the E-shaped core 51, the leakage flux φd generated in the defect portion 14 can be detected efficiently when a member having a large initial magnetic permeability $\mu_i$ is used.

FIG. 15 is a characteristic graph showing the detection sensitivity of the magnetic sensor versus the magnetic pole distance of the E-shaped core 51. This graph shows the detection sensitivity in the case where an artificial defect portion 14 is flaw-detected while the sectional area (thickness E) of each of the magnetic poles 51a, 51b and 51c in the E-shaped core 51 is changed.

As is obvious from the aforementioned expression (2), there is obtained characteristic in which the sensitivity for detection of the artificial defect portion 14 is substantially proportional to the magnetic pole thickness E because the magnetic reluctance $R_\phi$ in the E-shaped core 51 decreases. Incidentally, the distance (in the direction of the movement of the subject steel plate 13) where the magnetic flux φd generated from the artificial defect portion 14 is crossing the E-shaped core 51 increases as the magnetic pole thickness E increases.

In this case, a signal obtained by detection of leakage flux from the artificial defect portion 14 becomes also long (broad) proportionally to the magnetic pole thickness E of the E-shaped core 51, and the frequency of the defect signal therefore becomes low when flaw detection is performed while the moving speed of the subject steel plate 13 is kept constant. By increasing the magnetic pole thickness E of the E-shaped core 51, the magnetic reluctance $R_\phi$ of the E-shaped core 51 is reduced so that the relative detection sensitivity with respect to the artificial defect portion 14 increases. Because the frequency of the defect signal, however, moves into a lower range, noise cannot be separated when the frequency of the defect signal approaches the frequency of a noise voltage generated on the basis of various kinds of noise (local change in plate thickness, mechanical distortion, etc.) existing in the subject steel plate 13. Accordingly, the increase of the magnetic pole thickness E of the E-shaped core 51 is not always advantageous.

FIG. 16 is an external appearance view of the E-shaped magnetic sensor 50 disposed on an upper portion of the subject steel plate 13. In the drawing, the E-shaped magnetic sensor 50 is symmetrically shaped in the same manner as in the embodiment of FIG. 5, and the thicknesses of the magnetic poles are equal to each other. The distance between the magnetic poles is made D, the thickness of each of the magnetic poles is made E, and the width of the E-shaped core 51 is made W. Further, the distance between the subject steel plate 13 and the E-shaped magnetic sensor 50, that is, the liftoff is made L.

Figure 17A:
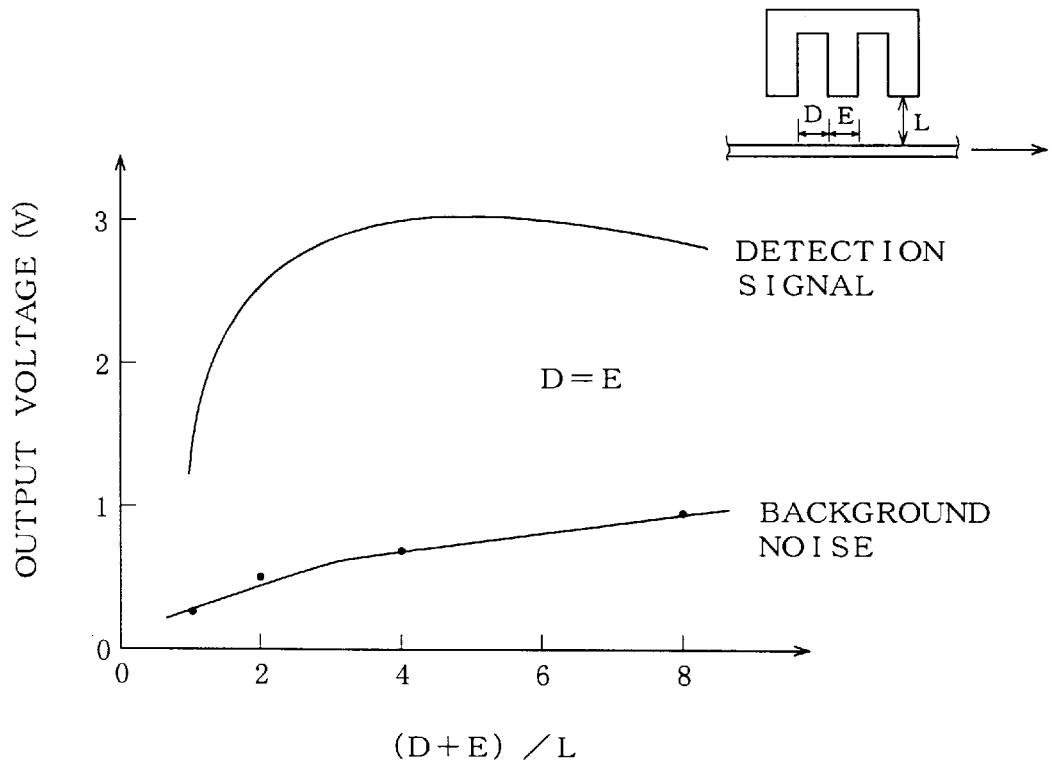
FIG. 17A is a characteristic graph showing the influence of (D+E)/L on a detection signal from a defect of about $10^{-3}$ ($mm^3$) in the subject steel plate 13 and the background noise.

FIG. 17A is a characteristic view showing the influence of (D+E)/L on a signal obtained by detection of a defect of about $10^{-3}$ (mm$^3$) in the subject steel plate 13 and on background noise. The background noise increases gradually as (D+E)/L increases. This is considered to be a tendency that background noise is picked up easily because the detection area of the E-shaped magnetic sensor 50 increases as (D+E)/L increases. On the other hand, the detection signal has a tendency that the signal increases rapidly before (D+E)/L reaches 4 and then decreases gradually. This is considered as follows. It is considered that, when (D+E)/L is too small, the output voltage of the detection signal in the search coil 52 decreases so that the detection efficiency is lowered because the local leakage flux from the defect portion 14 of the subject steel plate 13 is inputted into both the magnetic circuit constituted by the left and center magnetic poles 51a and 51b and the magnetic circuit constituted by the right and center magnetic poles 51c and 51b so as to be canceled partially. It is considered that, when (D+E)/L is contrariwise too large, the change of magnetic flux in the search coil 52 in the case where the defect portion 14 of the subject steel plate 13 runs just under the E-shaped magnetic sensor 50 decreases.

Figure 17B:
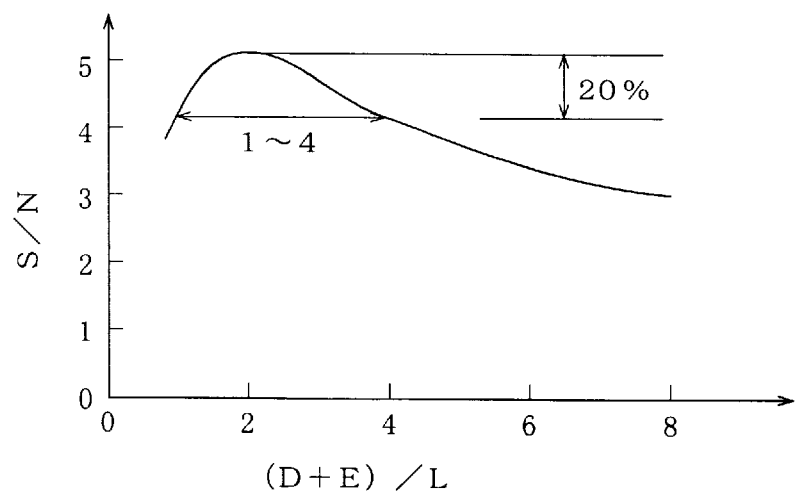
FIG. 17B is a characteristic graph showing S/N in the case where (D+E)/L is changed.

FIG. 17B is a characteristic graph showing S/N in the case where (D+E)/L is changed. From the aforementioned reason, as shown in FIG. 17B, there is an optimum range for maximizing S/N when (D+E)/L is changed. Practically, it is efficient to use it in a range of S/N from the maximum value thereof to a value reduced by about 20% from its maximum value. Accordingly, the size of the E-shaped magnetic sensor is preferably selected to satisfy the following expression (3).

$$1 < (D+E)/L < 4 \qquad (3)$$

Figure 18:
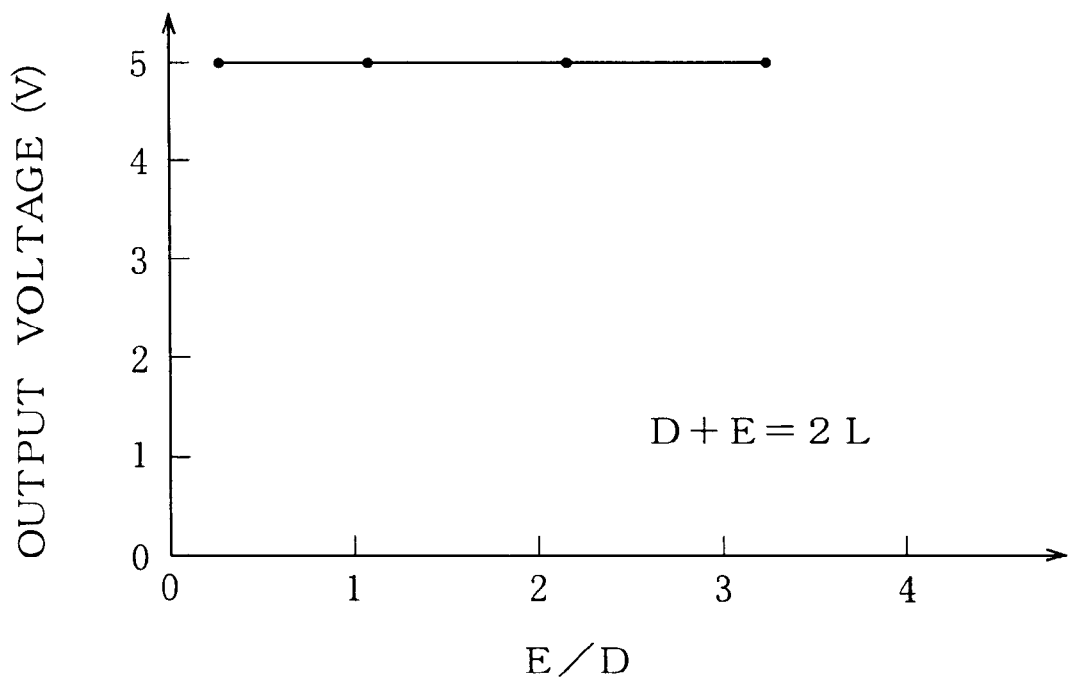
FIG. 18 is a characteristic graph showing the change of an output voltage of the E-shaped magnetic sensor in the case where (D+E) is kept constant and where the ratio E/D of the magnetic pole thickness E to the magnetic pole distance D is changed.

FIG. 18 is a characteristic graph showing the change of the output voltage of the E-shaped magnetic sensor 50 in the case where the ratio E/D of the magnetic pole thickness E to the magnetic pole distance D is changed while (D+E) is kept constant. It is apparent that the output voltage little changes even in the case where E/D is changed. Practically, however, there are problems that machining becomes difficult, magnetic saturation occurs easily, etc. when the magnetic pole thickness is too small, while there are also problems that the winding of the search coil becomes difficult, etc. when the magnetic pole thickness is too large and the magnetic pole distance is too small. Accordingly, the ratio of E to D is generally taken in a range for easy production.

Figure 19A:
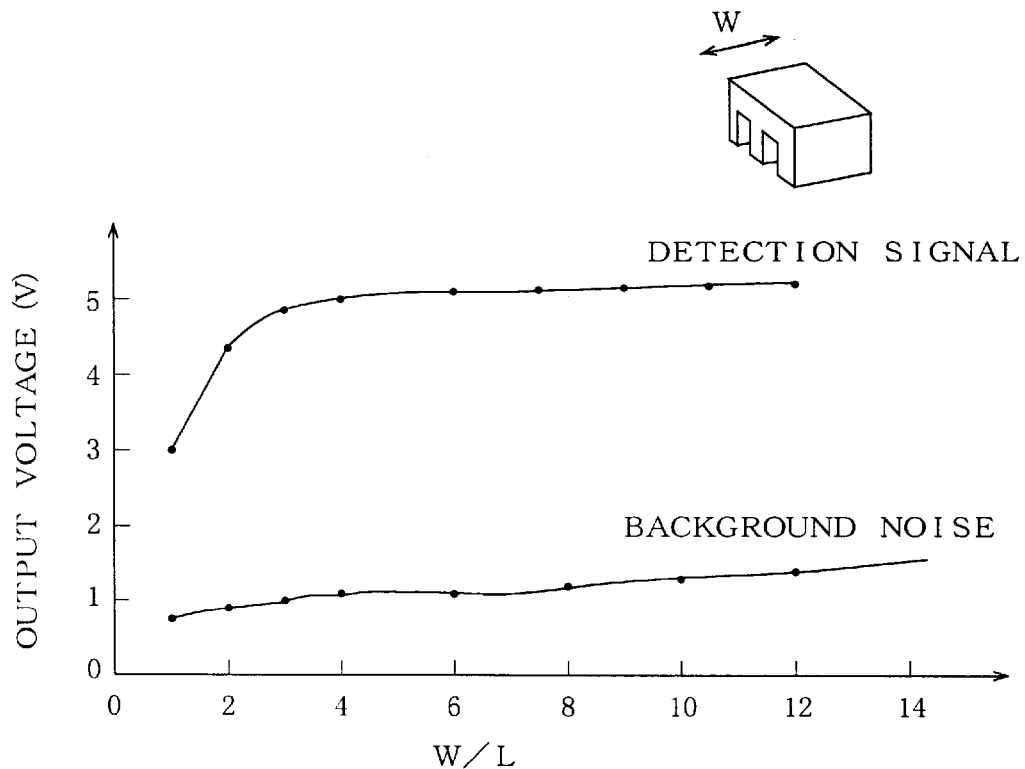
FIG. 19A is a characteristic graph showing the relation of a detection signal from a defect of about $10^{-3}$ ($mm^3$) in the subject steel plate and the background noise with respect to W/L.
Figure 19B:
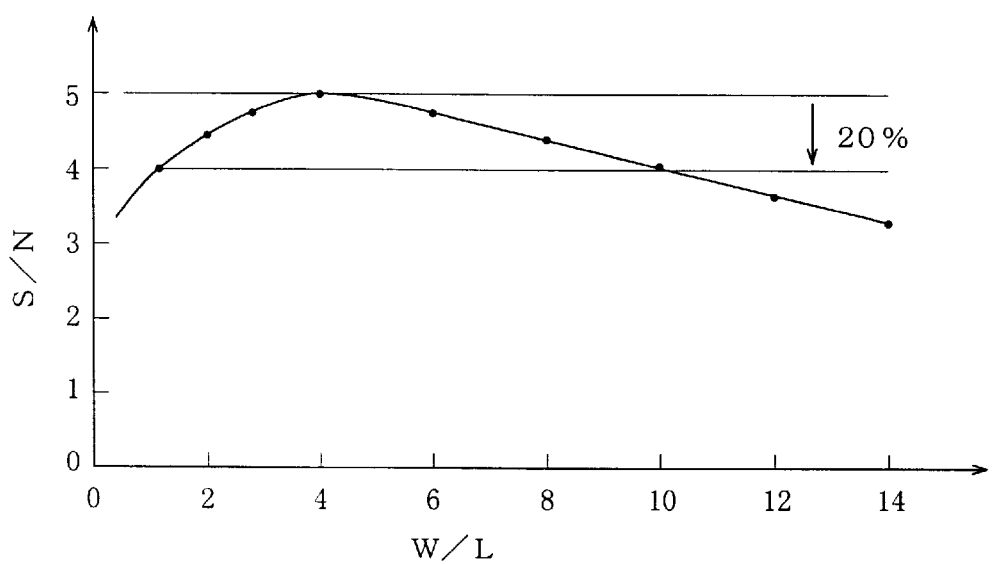
FIG. 19B is a characteristic graph showing S/N in the case where W/L is changed.

FIG. 19A is a characteristic graph showing the relation of a signal obtained by detection of a defect of about $10^{-3}$ (mm$^3$) in the subject steel plate 13 and background noise with respect to W/L. If the width W of the E-shaped magnetic sensor 51 is too small, the sectional area of the search coil 52 decreases and the detection voltage decreases so that the detection efficiency is lowered. When the sensor width W becomes large and reaches a certain value, the distribution of local leakage flux from the micro defect portion 14 is covered substantially by the sensor so that the output voltage is not increased any more even if the sensor width W is increased. If the sensor width W contrariwise becomes large, the detection range just under the E-shaped magnetic sensor 51 is widened so that the background noise increases because there is a tendency that noise is taken up easily. Accordingly, as shown in FIG. 19B, there is an optimum range in which S/N is maximized when W/L is changed. Practically, it is efficient to use it in a range of S/N from the maximum value thereof to a value reduced by 20% from the maximum value. Accordingly, from FIG. 19B, the following expression is preferably given.

$$1 < W/L < 10 \qquad (4)$$

Further, if an intensive floating magnetic field from the magnetizer becomes large, there is a risk that the core (especially the magnetic poles 51a and 51c) of the E-shaped magnetic sensor having a shape through which magnetic flux passes easily is magnetically saturated. To prevent this phenomenon and to cut off the external magnetic noise, a magnetic shielding plate 56 of a ferromagnetic substance is preferably arranged in the outside of the E-shaped magnetic sensor 50 as shown in FIG. 20. For example, this magnetic shielding plate 56 is constituted by a ferromagnetic core.

Reduction of the distance between the magnetic shielding plate 56 and the E-shaped core 51 as sufficiently as possible is preferably required for reduction of the size of the E-shaped magnetic sensor 50. However, if the magnetic shielding plate 56 and the E-shaped core 51 come too close to each other, the floating magnetic field absorbed by the shielding plate 56 flows into the E-shaped core 51 to bring a bad influence. Therefore, it is effective that a necessary but smallest magnetic reluctance portion is formed between the magnetic shielding plate 56 and the E-shaped core 51. Because the relative permeability of the magnetic substance is generally in a range from 100 to 1000 and the relative permeability of air is 1, a gap having magnetic reluctance about 10 times as much as the magnetic reluctance in the magnetic shielding may be preferably formed. It is, therefore, necessary that the gap Gs between the magnetic shielding plate 56 and the E-shaped core 51 is selected to be not smaller than about 1/10 the thickness S of the magnetic shielding plate 56. Accordingly, the following expression is preferably given.

$$S/10 < Gs \qquad (5)$$

Figure 21A:
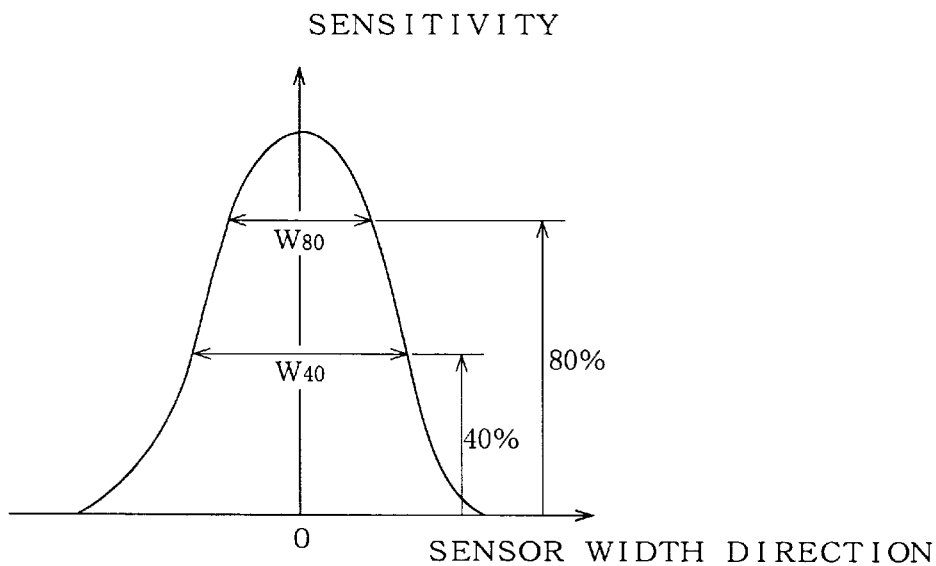
FIG. 21A is a characteristic graph showing detection sensitivity in the width direction of the E-shaped magnetic sensor with respect to a defect of about $10^{-3}$ (mm$^3$)
Figure 21B:
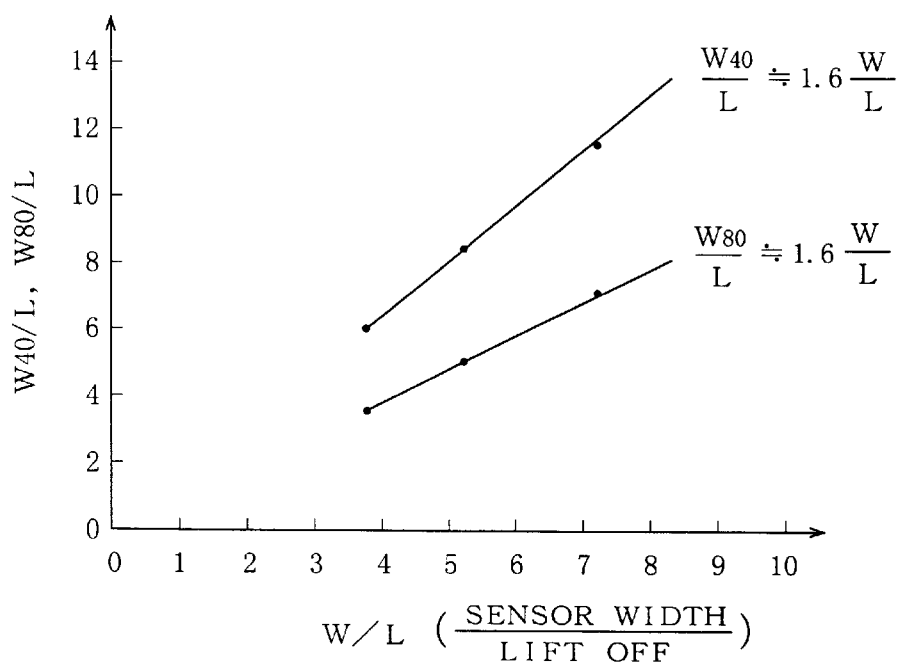
FIG. 21B is a characteristic graph showing detection sensitivity versus the ratio W/L of sensor width W to liftoff L.

FIG. 21A is a characteristic graph showing the detection sensitivity in the width direction of the E-shaped magnetic sensor 50 with respect to a defect of about $10^{-3}$ (mm$^3$). When the width in which widthwise sensitivity of 80% with respect to its maximum value is obtained is made W80 and the width in which widthwise sensitivity of 40% with respect to its maximum value is obtained is made W40 as shown in FIG. 21A, characteristic as shown in FIG. 21B is obtained with respect to the ratio W/L of the sensor width W to the liftoff L.

Figure 22A:
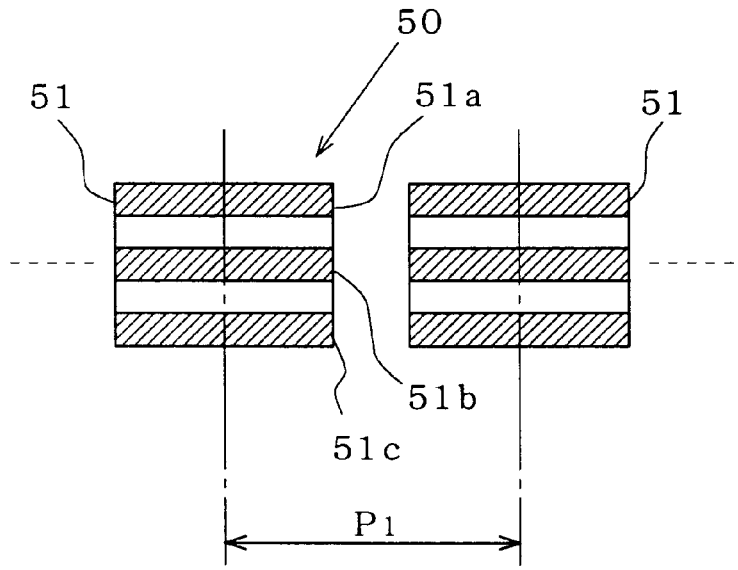
FIGS 22A and 22B are explanatory views showing examples of arrangement of the E-shaped magnetic sensor.
Figure 22B:
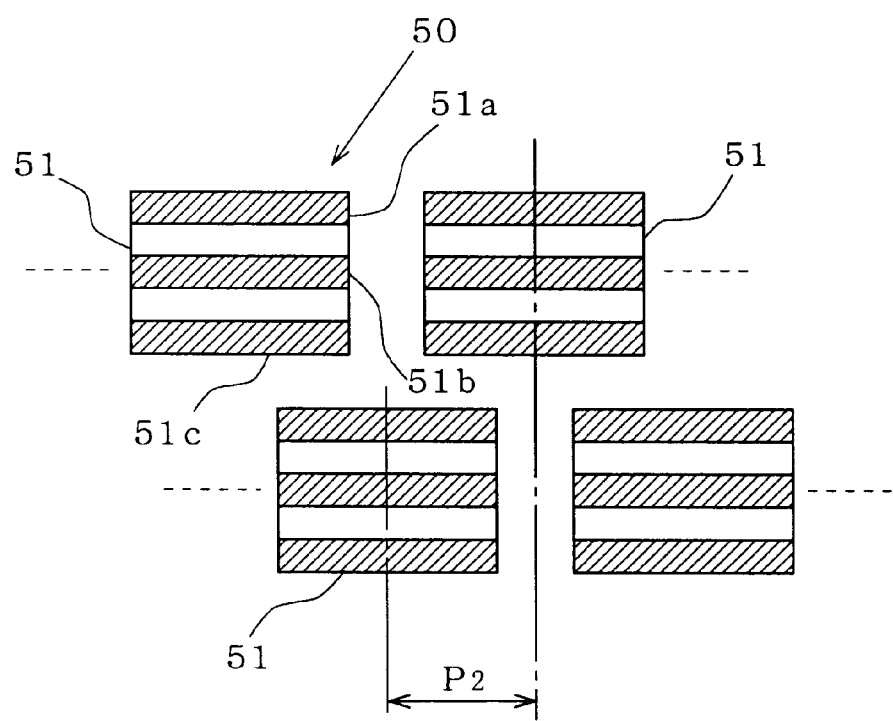

FIGS. 22A and 22B are explanatory views showing examples of arrangement of E-shaped magnetic sensors 50. When E-shaped magnetic sensors 50 are arranged in line so that outputs of adjacent E-shaped magnetic sensors 50 are added up in order to cover flaw detection in the width direction of the steel belt as shown in FIG. 22A, the sensors 50 are compensated by each other so that a uniform sensitivity distribution in a predetermined range in the width direction of the steel belt is obtained. If the dropping of the sensitivity distribution in the width direction of the subject steel plate 13 is allowed up to 20% so that the number of E-shaped magnetic sensors 50 is reduced as sufficiently as possible from the point of view of practical use, the sensitivity of one E-shaped magnetic sensor can be reduced to 40%. Accordingly, from the characteristic of FIG. 21B, the pitch P1 between the E-shaped magnetic sensors is preferably selected to satisfy the following expression.

$$P1 < 1.6W \qquad (6)$$

When outputs of adjacent E-shaped magnetic sensors 50 are added up, the range covered by the E-shaped magnetic sensors 50 is widened, but S/N is worsened because noise components are added up so that the amplitude of noise is increased to $\sqrt{2}$ times. When it is necessary to avoid the lowering of S/N, an operation in which outputs of two E-shaped magnetic sensors are compared with each other sequentially and a larger one of the output signals is used, that is, an OR operation may be performed. In this case, however, because the signal is not added, the dropping of the sensitivity between the E-shaped magnetic sensors 50 is not improved. Therefore, it is necessary to reduce the distance between the E-shaped magnetic sensors 50 to narrow the range in which the sensitivity is lowered. In this case, in order to suppress the dropping of sensitivity to be within 20% at maximum, it is necessary from the characteristic of FIG. 21B that the pitch between the E-shaped magnetic sensors 50 is selected to be 0.9W/L. To achieve this condition, the E-shaped magnetic sensors 50 are preferably arranged zigzag so as to overlap each other in the width direction as shown in FIG. 22B. Accordingly, the pitch P2 between the E-shaped magnetic sensors 50 is preferably selected as follows.

$$P2<0.9W \tag{7}$$

That is, in the case where a slight lowering of S/N is allowed, E-shaped magnetic sensors 50 are preferably arranged in line as an array (FIG. 22A) so that outputs of adjacent sensors are added up. On the other hand, in order to perform detection without lowering of S/N as sufficiently as possible, it is preferable to arrange E-shaped magnetic sensors 50 zigzag (FIG. 22B) and an OR operation is performed on the outputs of sensors which overlap each other in the width direction.

Figure 23:
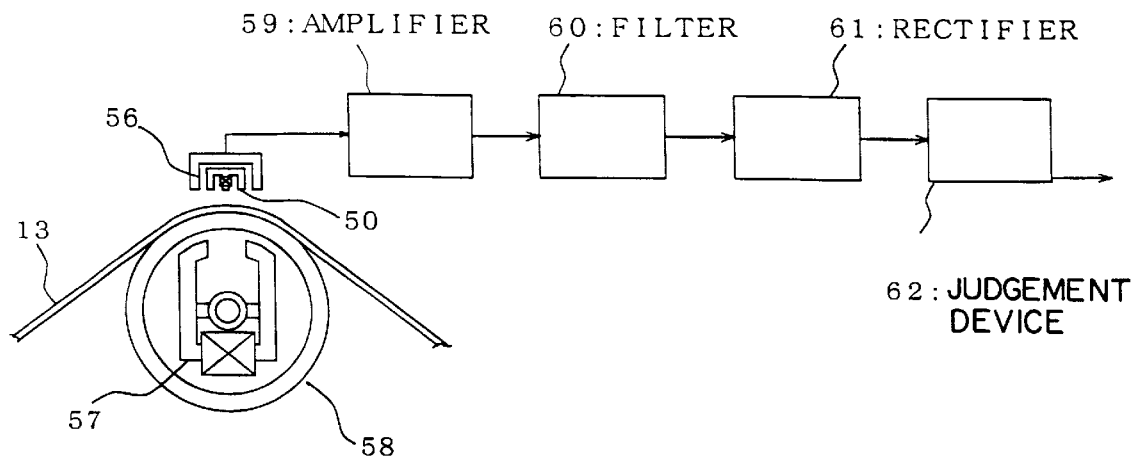
FIG. 23 is a block diagram showing the configuration of the magnetic flaw detection apparatus according to an embodiment of the present invention.

FIG. 23 is a block diagram showing the configuration of the magnetic flaw detection apparatus according to an embodiment of the present invention. In the drawing, the reference numeral 57 designates a magnetizer; 58, a nonmagnetic roll; 59, an amplifier; 60, a filter; 61, a rectifier; and 62, a judgment circuit. The magnetizer 57 having an electromagnet is arranged in the nonmagnetic roll 58 so that the subject steel plate (thin steel belt) 13 running on the nonmagnetic roll 58 is magnetized in the direction of the running thereof through the nonmagnetic roll 58. The aforementioned E-shaped magnetic sensor 50 is arranged above the nonmagnetic roll 58. When the subject steel plate 13 runs and a micro inclusion is present in the inside of the subject steel plate 13, weak leakage flux is generated locally therefrom. When this leakage flux passes just under the E-shaped shaped magnetic sensor 50, an electric signal corresponding to the leakage flux is outputted from the E-shaped magnetic sensor 50 as described above. The output from the E-shaped magnetic sensor 50 is electrically amplified by the amplifier 59 and noise is suppressed through the filter 60 to improve S/N. After the electric signal is then rectified by the rectifier 61, a defect is judged by the judgment circuit 62 and the result of the judgment is outputted.

In this embodiment, the liftoff L between the subject steel plate 13 and the E-shaped magnetic sensor 50, and the magnetic pole distance D, magnetic pole thickness E and sensor width W in the E-shaped magnetic sensor 50 are selected so as to be L=0.5 (mm), D=0.5 (mm), E=0.4 (mm) and W=3.5 (mm), respectively. Further, a magnetic shielding plate 56 of permalloy having a thickness S=2 (mm) is provided on the outside of the E-shaped magnetic sensor 50 so that a gap Gs=0.5 (mm) is formed between the magnetic shielding plate 56 and the sensor. As a sensor head, 220 E-shaped magnetic sensors 50 are arranged in line in the width direction of the steel plate in order to perform flaw detection on the whole width 1100 (mm) of the subject steel plate, and the pitch P1 between adjacent E-shaped magnetic sensors 50 is selected to be 5 (mm) so that outputs of adjacent E-shaped magnetic sensors are added up so as to be used for detection. That is, the distance between the E-shaped magnetic sensors 50 is 3.5 (mm).

The addition of the outputs of the E-shaped magnetic sensors 50 is performed after the amplifier 59. The addition may be performed after the filter 60 but preferably performed before the rectifier 61. This is because signal components can be added up simply whether the addition is performed after or before the rectifier 61, but noise components are added up to $\sqrt{2}$ times when the addition is performed before the rectifier and noise components are added up to 2 times when the addition is performed after the rectifier 61 and, as a result, S/N in the latter becomes lower. Stainless steel is used as the material for the nonmagnetic roll 58 and the force of magnetization of the magnetizer 57 in the nonmagnetic roll 58 is selected to be 3000 (AT). The moving speed of the subject steel plate (thin steel belt) is 300 (m/min). Further, as the filter 60, there is used a high-pass filter having a cutoff frequency of 3 kHz.

Figure 24:
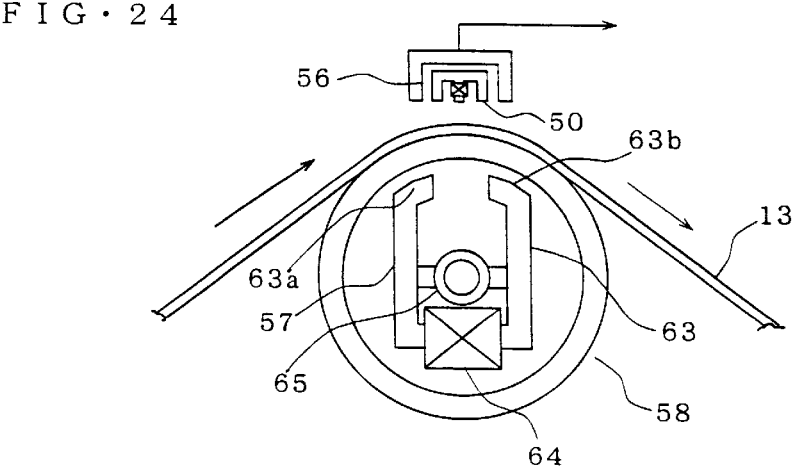
FIG. 24 is an explanatory view showing the detail of the magnetizer.

FIG. 24 is an explanatory view showing the detail of the magnetizer 57. As shown in the drawing, this magnetizer 57 has a magnetic core 63 formed with a pair of magnetizing magnetic poles 63a and 63b, and a coil 64. The magnetizer 57 is fixed to a shaft bearing 65. In this shaft bearing 65, the nonmagnetic roll 58 is rotatably supported. By supplying a direct current to the coil 64, magnetic flux is generated from the magnetizing magnetic poles 63a and 63b so that the subject steel plate 13 moving while wound on the nonmagnetic roll 58 is magnetized in the rolling direction by the magnetic flux.

Figure 25:
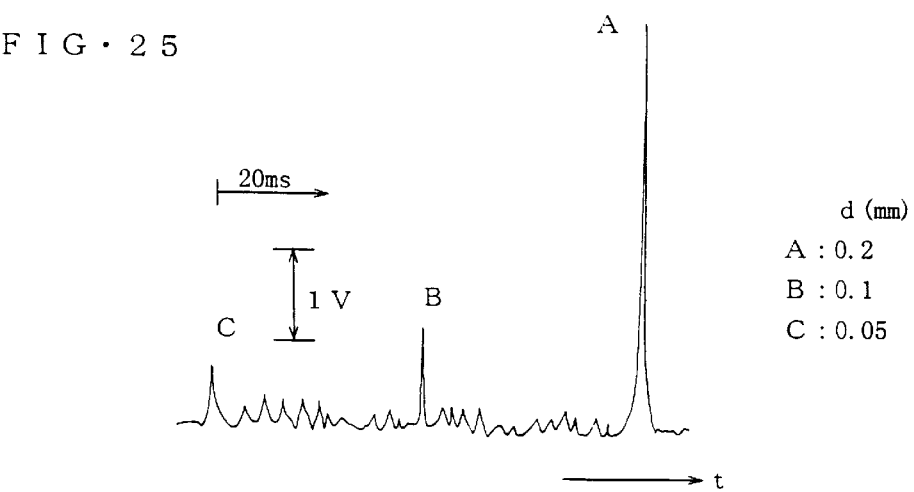
FIG. 25 is a graph showing the waveform of an artificial defect detected by the flaw detection apparatus according to the embodiment of FIG. 23.

FIG. 25 is a graph showing waveforms (output waveforms from the rectifier 61) of artificial defects detected by the flaw detection apparatus according to the aforementioned embodiment. This graph shows output waveforms in the case where artificial defects obtained by machining drill holes having hole diameters of 0.5, 0.1 and 0.2 (mm) respectively in a thin steel plate are flaw-detected. It is apparent from FIG. 25 that a micro defect can be detected with high S/N.

Figure 26:
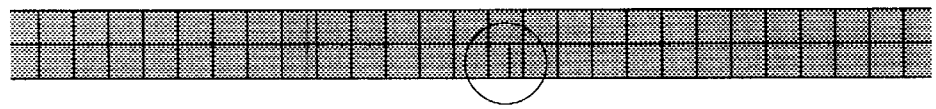
FIG. 26 is a graph showing a waveform in the case where a natural defect is detected.

Further, FIG. 26 is a graph showing a waveform in the case where a natural defect is detected. After flaw detection, the defect portion is cut out, and the size thereof is checked with a microscope while the fault portion is polished. As a result, there is an inclusion having a size of about $5\times10^{-4}$ ($mm^3$).

The optimum cutoff frequency of the filter 60 is 3 kHz. This value is as large as two or three times the optimum value in the case of use of a conventional magnetic sensor. Accordingly, background noise containing a large amount of low frequency components can be separated from the detection signal easily, so that S/N is improved greatly.

When the magnetic shielding plate 56 disposed on the outside of the E-shaped core 51 is removed, the E-shaped magnetic sensor 50 is magnetically saturated so that the sensitivity oi the sensor is lowered. Therefore, the E-shaped magnetic sensor 50 is used with the force of magnetization reduced to 2000 AT so that the E-shaped magnetic sensor 50 is not saturated, but an artificial defect prepared by a drill hole having a hole size of 0.05 (mm) cannot be detected in this case.

Figure 27A:
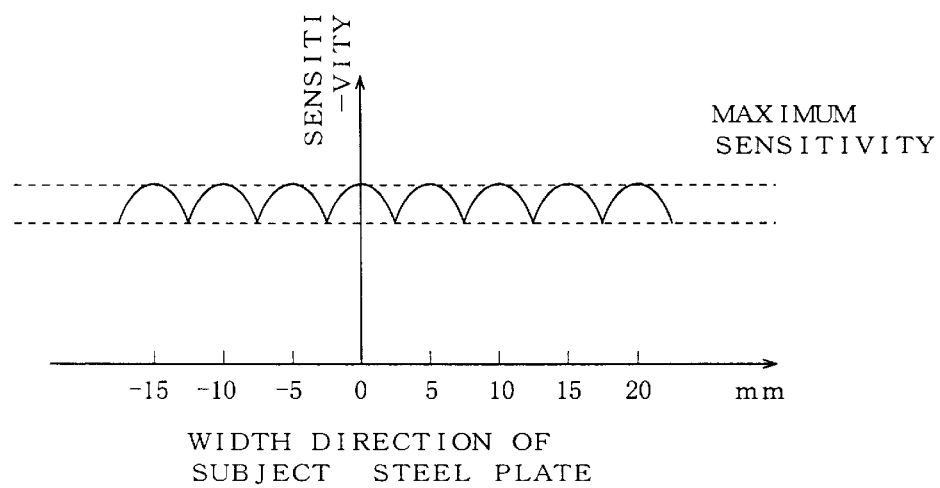
FIG. 27A is a characteristic graph showing the sensitivity distribution in the width direction of the subject steel plate in the magnetic flaw detection apparatus (sensor array arrangement) according to the embodiment of FIG. 23.

FIG. 27A is a characteristic graph showing the distribution of sensitivity in the width direction of the subject steel plate in the magnetic flaw detection apparatus according to this embodiment. The horizontal axis shows distance Y (mm) in the width direction and the vertical axis shows the relative value of sensitivity. Because the pitch of arrangement of the E-shaped magnetic sensors 50 is 5 (mm), sensitivity is maximized at intervals of 5 (mm) and minimized in the middle between the E-shaped magnetic sensors 50, but the lowering of sensitivity is suppressed within 20%.

Figure 27B:
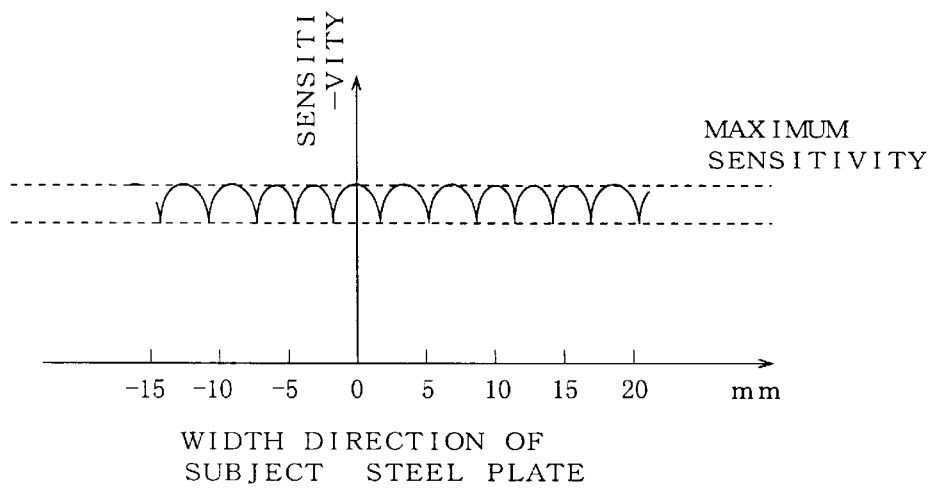
FIG. 27B is a characteristic graph showing the sensitivity distribution in the width direction of the subject steel plate in the magnetic flaw detection apparatus (zigzag arrangement) according to the embodiment of FIG. 23.

Further, as a substitute for the aforementioned sensor heads, two sensor arrays each prepared by arranging 183 E-shaped magnetic sensors with a magnetic pole distance D=0.5 (mm), a magnetic pole thickness E=0.4 (mm), a sensor width W=3.5 (mm) and a sensor distance of 2.5 (mm) in line are arranged zigzag, and this sensor group is magnetically shielded as a whole. In this case, the width of overlapping of sensors is 0.5 (mm). Further, in the case of zigzag arrangement of the sensors, a signal obtained by OR operation of the outputs of the overlapping sensors is used. In this case, the sensitivity distribution in the width direction of the steel belt is as shown in FIG. 27B, and the dropping of sensitivity with respect to the maximum sensitivity is suppressed to about 20%.

Although this embodiment shows the case where the sectional shape of each of the magnetic poles in the E-shaped magnetic sensor 50 is oblong, the effect is the same also in the case where the sectional shape is rounded by chamfering.

Separation of the background noise and the defect detection signal will be discussed below.

Figure 28:
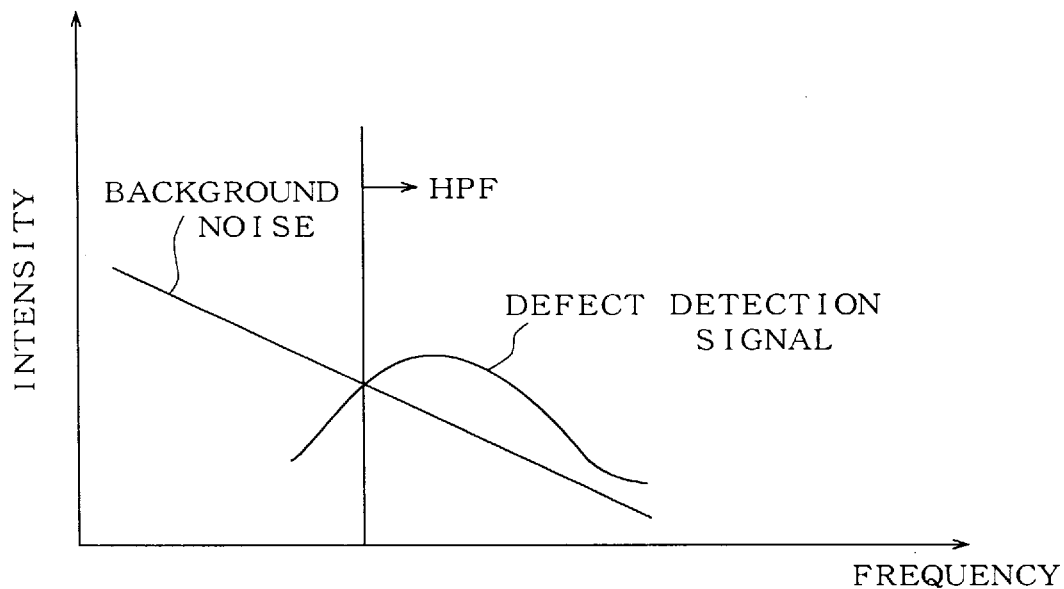
FIG. 28 is a characteristic graph showing the intensity of the frequency component of a defect signal and the background noise in the detection signal in the case where the E-shaped magnetic sensor is used.

FIG. 28 is a characteristic graph showing the intensity of the frequency component of the defect signal and the intensity of the frequency component of the background noise in the detection signal in the case where the E-shaped magnetic sensor is used. The background noise contains a large amount of low frequency components whereas the defect signal has a peak in a specific frequency. Accordingly, it is apparent that S/N can be improved when the low frequency components are removed by the high-pass filter 60.

Figure 29:
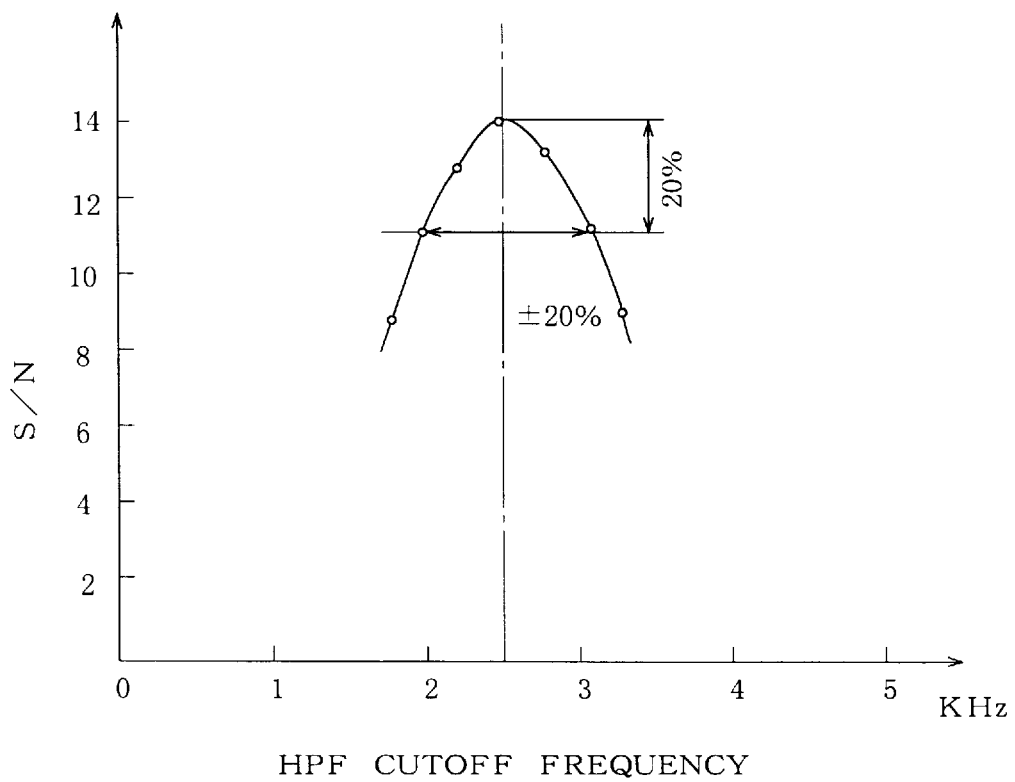
FIG. 29 is a characteristic graph showing an example of the change of S/N in the case where the cutoff frequency of the high-pass filter is changed.

FIG. 29 is a characteristic graph showing an example of the change of S/N in the case where the cutoff frequency of the high-pass filter 60 is changed. According to the characteristic, there is an optimum cutoff frequency in which S/N is maximized and, when the cutoff frequency is departed by ±20% from this optimum cutoff frequency, S/N is reduced by 20%. Accordingly, if reduction of S/N up to 20% with respect to the maximum value of S/N is allowed, cutoff frequencies in the range up to ±20% from the optimum cutoff frequency can be used.

Figure 30:
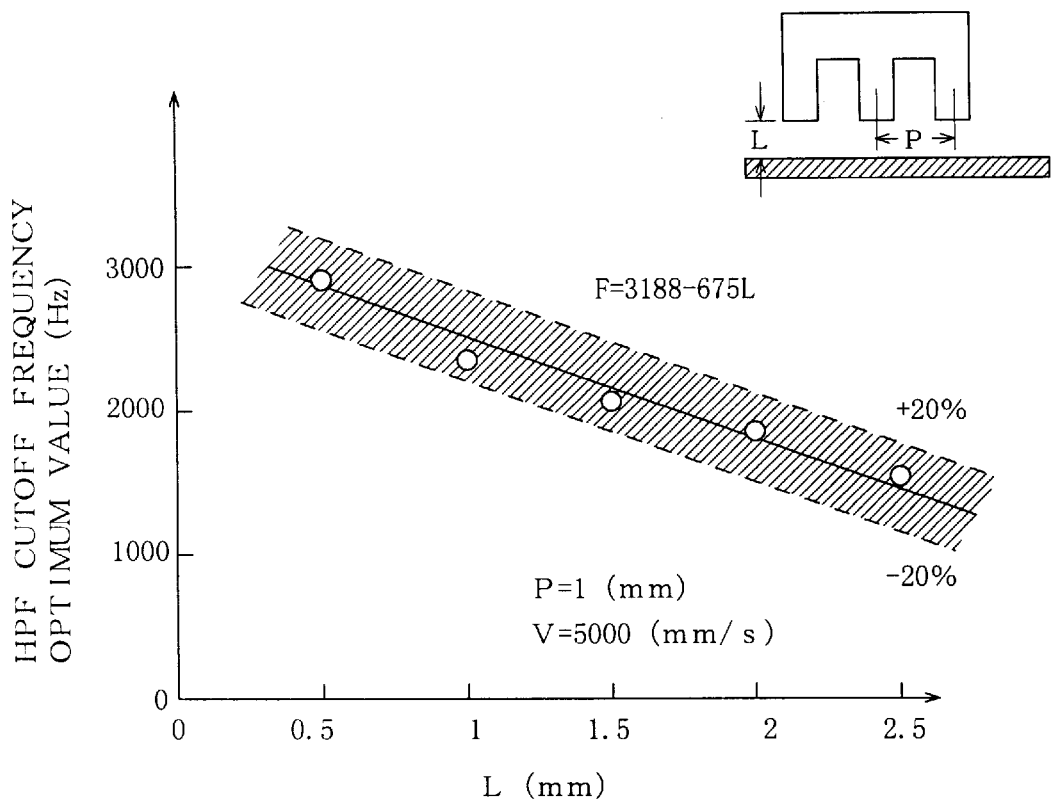
FIG. 30 is a characteristic graph showing the optimum cutoff frequency F (Hz) of the high-pass filter for maximizing S/N in the case where the magnetic pole size of the E-shaped magnetic sensor is kept constant and where the liftoff L (mm) is changed.

FIG. 30 is a characteristic graph showing the optimum cutoff frequency F (Hz) of the high-pass filter 60 in which S/N is maximized, when the liftoff L (mm) is changed and the magnetic pole size of the E-shaped magnetic sensor 50 is kept constant. When the running speed V of the subject steel plate 13 and the pitch between the centers of the magnetic poles in the E-shaped magnetic sensor 50 are set to be V=5000 (mm/s) and P=1 (mm) respectively, F=3188−657L is obtained.

Figure 31:
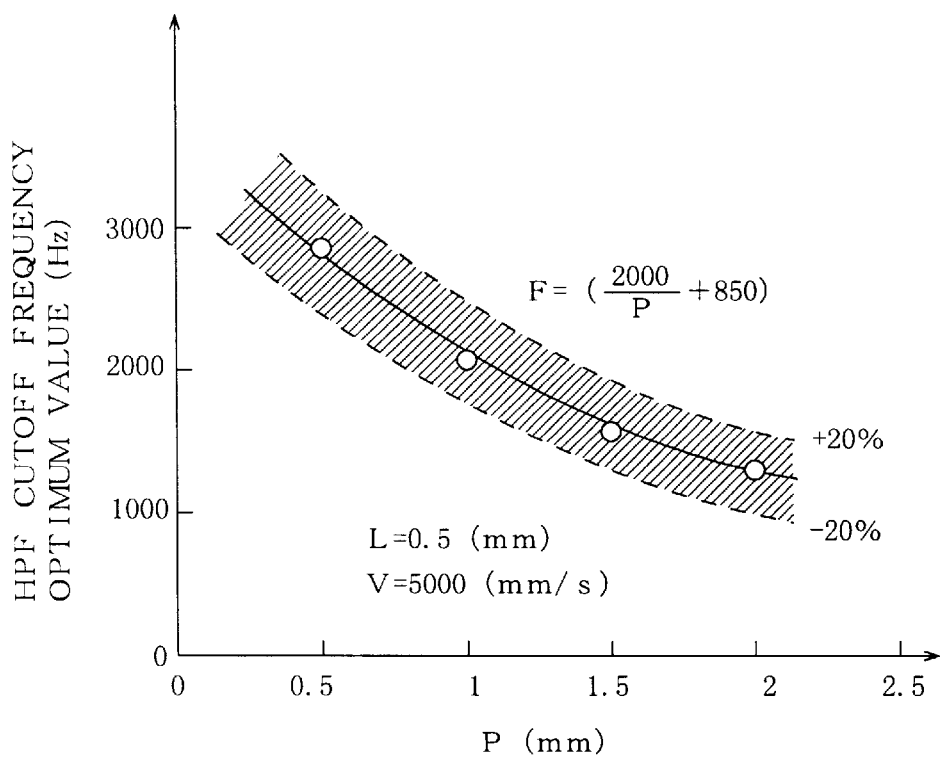
FIG. 31 is a characteristic graph showing the optimum cutoff frequency F (Hz) of the high-pass filter for maximizing S/N in the case where the liftoff L is kept constant and where the distance P (mm) between the centers of magnetic poles in the E-shaped magnetic sensor is changed.

FIG. 31 is a characteristic graph showing the optimum cutoff frequency F (Hz) of the high-pass filter 60 in which S/N is maximized, when the pitch P (mm) between the centers of the magnetic poles in the E-shaped sensor is changed and the liftoff L is kept constant. When the liftoff L and the running speed V of the subject steel plate 13 are set to be L=0.5 (mm) and V=5000 (mm/s) respectively, F=(850+2000/P) is obtained. It is thought of that the optimum cutoff frequency F (Hz) of the high-pass filter to maximize S/N is proportional to the moving speed V of the subject steel plate.

From these results, the optimum cutoff frequency F is given as follows.

$$F=V\times(3188-675L)\times(850+2000/P)/(1.4\times10^7) \quad (8)$$

It is further thought of that the allowed values with respect to the optimum value of the cutoff frequency F are within a range of ±20% as described above.

Figure 32:
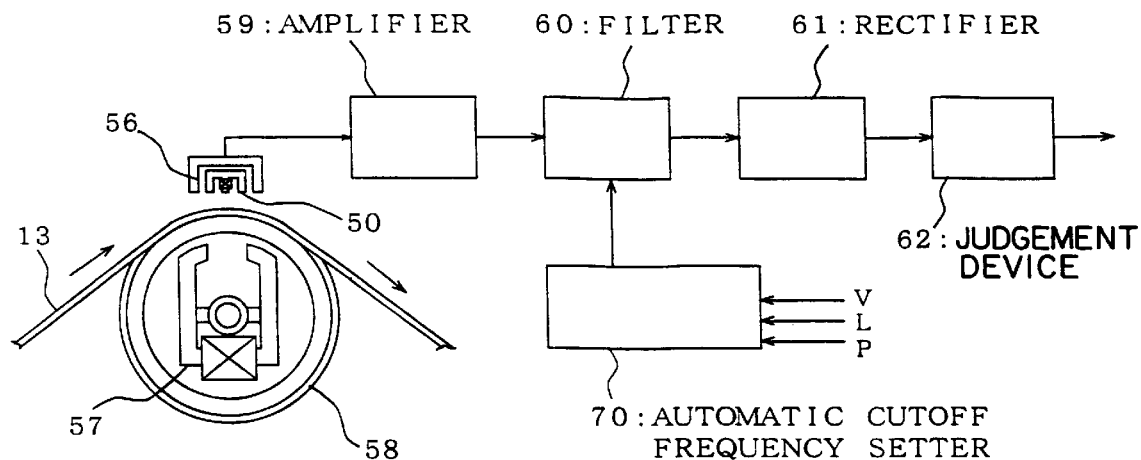
FIG. 32 is a block diagram showing the configuration of the magnetic flaw detection apparatus according to an embodiment in which the aforementioned cutoff frequency F is designed so as to be able to be changed correspondingly to the condition of the flaw detection.

FIG. 32 is a block diagram showing the configuration of the magnetic flaw detection apparatus according to an embodiment in which the aforementioned cutoff frequency F can be changed correspondingly to the flaw detection condition. This magnetic flaw detection apparatus is configured by adding an automatic cutoff frequency setter 70 to the flaw detection apparatus of FIG. 23.

The automatic cutoff frequency setter 70 reads the pitch P between the centers of the magnetic poles of the E-shaped magnetic sensor 50, the liftoff L and the moving speed V of the subject steel plate 13, performs calculation given by the aforementioned expression (8) to calculate the cutoff frequency and sets the thus obtained cutoff frequency to the high-pass filter 60. The calculation given by the expression (8) can be achieved easily when a micro-computer is used as the automatic cutoff frequency setter 70. In the case where the pitch P between the centers of the magnetic poles in the E-shaped magnetic sensor 50 is regarded as a fixed value or in the case where the liftoff L is regarded as a fixed value in addition to the pitch P, the fixed values may be set in the automatic cutoff frequency setter 13 in advance so that these values are not inputted from the outside.

Incidentally, also in this case, the E-shaped sensor 50 is preferably enclosed in the magnetic shielding plate 56 of a ferromagnetic substance so as to be magnetically shielded in order to reduce the influence of the floating magnetic field.

In the magnetic flaw detection apparatus configured as shown in FIG. 32, the liftoff L between the subject steel plate 13 and the E-shaped magnetic sensor 50 and the magnetic pole distance D, magnetic pole thickness E and sensor width W of the E-shaped magnetic sensor 50 are selected to be L=0.5 (mm), D=0.5 (m), E=0.4 (mm) and W=3.5 (mm) respectively. Further, a magnetic shielding plate 56 of permalloy having a thickness S=2 (mm) is provided in the outside of the E-shaped magnetic sensor 1 so that a gap Gs=0.5 (mm) is formed between the magnetic shielding plate 56 and the E-shaped magnetic sensor 50. Stainless steel is used as the material for the nonmagnetic roll 58, and the force of magnetization of the magnetizer 57 in the nonmagnetic roll 58 is selected to be 3000 AT. The running speed V of the subject steel belt (thin steel belt) is selected to be V=5000 (mm/s).

Furthermore, L, V and P are inputted into the automatic cutoff frequency setter 70, an arithmetic operation according to the expression (8) is performed and the result of the arithmetic operation is sent to the high-pass filter 60 so that the cutoff frequency of the high-pass filter is set to an optimum value automatically even in the case where the operating condition is changed. Incidentally, under the aforementioned condition, the cutoff frequency F of the high-pass filter is F=3000 (Hz).

Figure 33:
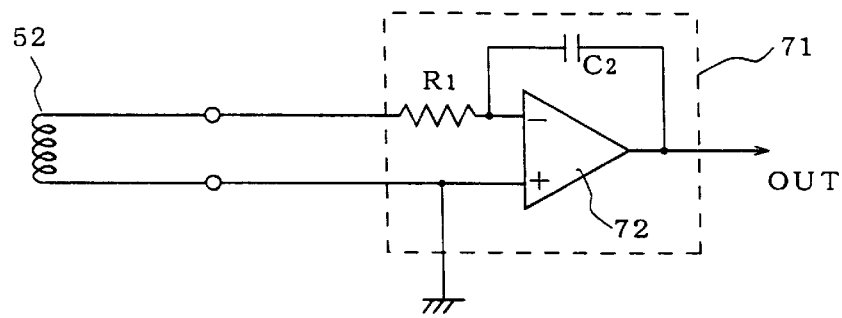
FIG. 33 is a circuit diagram of an integrating amplifier used as the amplifier depicted in FIGS. 23 and 32.

FIG. 33 is a circuit diagram of an integrating amplifier used for the amplifier 59 depicted in FIGS. 23 and 32. This integrating amplifier 71 is constituted by an integrating resistor $R_1$, a capacitor $C_2$, and an amplifier 72. When the defect signal detected by the search coil 52 of the E-shaped magnetic sensor 50 is amplified, an output voltage $e_0$ obtained in the search coil 52 is given as follows.

$$e_0 = \frac{d\phi d}{dt} \quad (V) \quad (9)$$

That is, the output voltage $e_0$ becomes an output inversely proportional to the absolute value of magnetic flux φd generated from the defect and the time required for making the defect 14 pass just under the search coil 52. Therefore, by using the integrating amplifier 71 as an amplifier which amplifies the output of the search coil 52, the output voltage of the same defect which increases proportionally to the moving speed of the subject steel plate 13 is compensated automatically so that a constant defect output of the amplifier can be obtained regardless of the moving speed of the subject steel plate.

Figure 34:
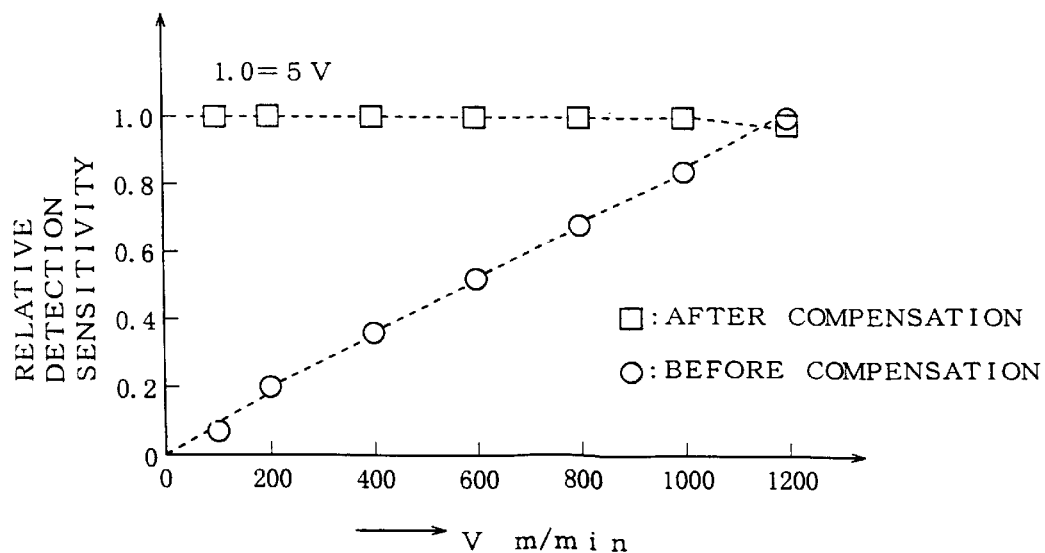
FIG. 34 is a characteristic graph showing detection sensitivity characteristic versus the moving speed of the subject steel plate in the case where a drill hole having a hole diameter of 0.1 (mm) is flaw-detected by using the integrating amplifier depicted in FIG. 33.

FIG. 34 is a characteristic graph showing detection sensitivity characteristic versus the moving speed of a ferromagnetic metal plate in the case where a drill hole having a hole diameter of 0.1 (mm) is flaw-detected by using the integrating amplifier 72 of FIG. 33. As shown in the drawing, difference in sensitivity for detection of the drill hole is suppressed within a range of 5% even in the case where the moving speed of the subject steel plate 13 is changed in a range from 10 to 1000 m/min.

We claim:

1. A magnetic flaw detection apparatus comprising:

a magnetizer for magnetizing a moving subject;

an E-shaped magnetic sensor including a core of a ferromagnetic substance, said core having an E-shape formed by a base portion and three projecting portions mounted on said base portion, said projecting portions constituting magnetic poles and being disposed facing said subject, said sensor further including a search coil wound on a center projecting portion of said three projecting portions for detecting magnetic flux generated due to a fault portion of said magnetized subject, said search coil providing an output signal when said magnetic flux is generated; and a high-pass filter having a predetermined cutoff frequency, F, for processing an output signal from said E-shaped magnetic sensor, said cutoff frequency being determined on the basis of the distance between the centers of said projecting portions, a liftoff which is the distance between said subject and said E-shaped core, and the moving speed of said subject.

2. A magnetic flaw detection apparatus according to claim 1, further comprising a shielding plate of a ferromagnetic substance for magnetically shielding said magnetic sensor.

3. A magnetic flaw detection apparatus according to claim 2, wherein: said magnetizer has a pair of magnetizing magnetic poles; and said E-shaped magnetic sensor is disposed between said pair of magnetizing magnetic poles.

4. A magnetic flaw detection apparatus according to claim 1 further comprising a shaft bearing for mounting said magnetizer, and a nonmagnetic roll, inside of which said magnetizer is disposed, rotatably supported by said shaft bearing, wherein said subject is moved on said nonmagnetic roll and said E-shaped magnetic sensor is disposed on the opposite side of said subject from said nonmagnetic roll.

5. A magnetic flaw detection apparatus according to claim 1, wherein: said subject is a strip and wherein a row of three magnetic poles of said E-shaped core is arranged along the direction of the movement of said strip.

6. A magnetic flaw detection apparatus according to claim 5 wherein each projecting portion of said sensor is equally spaced from adjacent portions and wherein said E-shaped magnetic sensor satisfies the following expression:

$$1<(D+E)/L<4$$

where L is a liftoff which is the distance between said strip and said E-shaped core, D is the distance between adjacent projecting portions and E is the thickness of each projecting portion.

7. A magnetic flaw detection apparatus according to claim 6, wherein said E-shaped magnetic sensor satisfies the following expression:

$$1<W/L$$

wherein W is the width of each projecting portion crossing said strip.

8. A magnetic flaw detection apparatus according to any claim 5, wherein said E-shaped core and said magnetic shielding plate are disposed so that a gap Gs between said E-shaped core and said magnetic shielding plate satisfies the following expression:

$$S/10<Gs$$

where S is the thickness of said shielding plate.

9. A magnetic flaw detection apparatus according to claim 5 wherein E-shaped magnetic sensors are aligned in the width direction of said strip at intervals of a pitch P1 which satisfies the following expression:

$$P1<1.6W$$

where W is the width of each projecting portion crossing said strip, and wherein outputs of said E-shaped sensors adjacent to each other are added up so as to be used for fault detection.

10. A magnetic flaw detection apparatus according to claim 5 wherein said E-shaped magnetic sensors are disposed zigzag in the width direction of said strip at intervals of a pitch P2 which satisfies the following expression:

$$P2<0.9W$$

where W is the width of each projecting portion crossing said strip, and wherein the larger one of said outputs of said E-shaped magnetic sensors overlapping each other in the width direction is used for fault detection.

11. A magnetic flaw detection apparatus according to claim 1, wherein said subject is a thin steel belt which moves; and said fault portion of said subject is a micro inclusion mixed in said thin steel belt.

12. A magnetic flaw detection flaw detection apparatus according to claim 1, further comprising a cutoff frequency setter for receiving the moving speed of said subject and a liftoff L which is the distance between said subject and said E-shaped core as input values, and determining and setting a cutoff frequency of said high-pass filter automatically.

13. A magnetic flaw detection apparatus according to claim 12, wherein said cutoff frequency setter sets said cutoff frequency F in a range of ±20% with reference to a frequency F (Hz) satisfying the following expression:

$$F=V\times(3188-675L)\times(850+2000/P)/(1.4\times10^7)$$

where P (mm) is the distance between the centers of said magnetic poles of the E-shaped magnetic sensor, L (mm) is said liftoff, and V (mm/s) is the moving speed of said subject.

14. A magnetic flaw detection apparatus according to claim 1, wherein said cutoff frequency F is set to be in a range of ±20% with reference to a frequency F (Hz) satisfying the following expression:

$$F=V\times(3188-675L)\times(850+2000/P)/(1.4\times10^7)$$

where P (mm) is the distance between the centers of each projecting portion, L (mm) is said liftoff, and V (mm/s) is the moving speed of said subject.

* * * * *